(12) United States Patent
Bold et al.

(10) Patent No.: US 7,846,763 B2
(45) Date of Patent: Dec. 7, 2010

(54) TRANSITION METAL COMPLEXES COMPRISING CARBENE LIGANDS SERVING AS EMITTERS FOR ORGANIC LIGHT-EMITTING DIODES (OLED'S)

(75) Inventors: Markus Bold, Dirmstein (DE);
Christian Lennartz, Neuhofen (DE);
Martina Prinz, Dossenheim (DE);
Hans-Werner Schmidt, Bayreuth (DE);
Mukundan Thelakkat, Bayreuth (DE);
Markus Baete, Kulmain (DE);
Christian Neuber, Bayreuth (DE);
Wolfgang Kowalsky, Braunschweig (DE); Christian Schildknecht, Braunschweig (DE); Hans-Hermann Johannes, Braunschweig (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1054 days.

(21) Appl. No.: 10/568,344

(22) PCT Filed: Aug. 18, 2004

(86) PCT No.: PCT/EP2004/009269

§ 371 (c)(1),
(2), (4) Date: Feb. 14, 2006

(87) PCT Pub. No.: WO2005/019373

PCT Pub. Date: Mar. 3, 2005

(65) Prior Publication Data
US 2006/0258043 A1      Nov. 16, 2006

(30) Foreign Application Priority Data
Aug. 19, 2003   (DE) ................. 103 38 550

(51) Int. Cl.
*H01L 51/40* (2006.01)
*C07F 15/00* (2006.01)
(52) U.S. Cl. ..................... 438/99; 548/103
(58) Field of Classification Search ............. 438/99; 548/103
See application file for complete search history.

(56) References Cited

U.S. PATENT DOCUMENTS

| | | | |
|---|---|---|---|
| 6,160,267 | A | 12/2000 | Kunugi et al. |
| 6,338,977 | B1 | 1/2002 | Kunugi et al. |
| 2002/0034656 | A1* | 3/2002 | Thompson et al. .......... 428/690 |

FOREIGN PATENT DOCUMENTS

| WO | 00/70655 | 11/2000 |
|---|---|---|
| WO | 01/41512 | 6/2001 |
| WO | 02/15645 | 2/2002 |

OTHER PUBLICATIONS

Hitchcock et al. Journal of Organometallic Chemistry, 1982, vol. 239, pp. C26-C30.*
Lai, Siu-Wai, et al., "Carbene and Isocyanide Ligation at Luminescent Cyclometalated 6-Phenyl-2,2'-bipyridyl Platinum (II) Complexes: Structural and Spectroscopic Studies", Organometallics, vol. 18, pp. 3327-3336, 1999.
Liu, Qing-Xiang et al., "Synthesis, crystal structure and photophysical properties of N-heterocyclic carbene Pd(II), Pt(II) complexes and iodine adduct", Polyhedron, vol. 22, pp. 1515-1521, 2003.
Lai, Siu-Wai et al., "Luminescent metal complexes derived from carbene and related ligands: tuning excited-state properties with metal-carbon multiple bonds", Journal of Organometallic Chemistry, vol. 617-618, pp. 133-140, 2001.
Lai, Siu-Wai et al., "[{Pt(CN) (C10H21N4)}6]: A Luminescent Hexanuclear Platinum (II) Macrocycle Containing Chelating Dicarbene and Bridging Cyanide Ligands", Angew. Chem. Int. Ed., vol. 37, No. ½, pp. 182-184, 1998.
Xue, Wen-Mei et al., "Spectroscopic and Excited-State Properties of Luminescent Rhenium (I) N-Heterocyclic Carbene Complexes Containing Aromatic Diimine Ligands", Organometallics, vol. 17, pp. 1622-1630, 1998.

(Continued)

*Primary Examiner*—Joseph R Kosack
(74) *Attorney, Agent, or Firm*—Oblon, Spivak, McClelland, Maier & Neustadt, L.L.P.

(57) ABSTRACT

Use of transition metal complexes of the formula (I) in organic light-emitting diodes

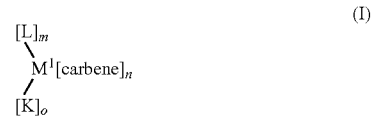

where:
$M^1$ is a metal atom;
carbene is a carbene ligand;
L is a monoanionic or dianionic ligand;
K is an uncharged monodentate or bidentate ligand selected from the group consisting of phosphines; CO; pyridines; nitrites and conjugated dienes which form a π complex with $M^1$;
n is the number of carbene ligands and is at least 1;
m is the number of ligands L, where m can be 0 or $\geq 1$;
o is the number of ligands K, where o can be 0 or $\geq 1$;
where the sum n+m+o is dependent on the oxidation state and coordination number of the metal atom and on the denticity of the ligands carbene, L and K and also on the charge on the ligands carbene and L, with the proviso that n is at least 1, and also
an OLED comprising these transition metal complexes, a light-emitting layer comprising these transition metal complexes, OLEDs comprising this light-emitting layer, devices comprising an OLED according to the present invention, and specific transition metal complexes comprising at least two carbene ligands.

16 Claims, 2 Drawing Sheets

OTHER PUBLICATIONS

Hitchcock, Peter B. et al., "Synthesis of Homoleptic Tris (organo-Chelate) Iridium (III) Complexes by Spontaneous ortho-Metallation of Electron-Rich Olefin-Derived N, N'-*Diarylcarbene Ligands* and the X-Ray *Structures of fac*-[Ir{CN(C6H4Me-p) (CH2)2 NC6H3Me-p}3] And Mer-[Ir {CN(C6H4Me-p) (CH2)2 NC6H3Me-p}2 {CN(C6H4Me-p) (CH2)2 NC6H4Me-p} ]Cl (A Product of HCl Cleavage)", Journal of Oraganometallic Chemistry, vol. 239, pp. C26-C30, 1982.

Gruendemann, Stephan et al., Abnormal Ligand Binding and Reversible Ring Hydrogenation in the Reaction of Imidazolium Salts with IrH5 (PPh3)2, J.Am. Chem., vol. 124, pp. 10473-10481, 2002.

Chianese, Anthony R. et al., "Rhodium and Iridium Complexes of N-heterocyclic Carbenes via Transmetalation: Structure and Dynamics", Organometallics, vol. 22, pp. 1663-1667, 2003.

Weskamp, Thomas et al., N-heterocyclic carbenes: novel ruthenium-alkylidene complexes, Journal of Organometallic Chemistry, vol. 582, pp. 362-365, 1999.

Coleman, Karl S. et al., "Silver (I) complex of a new imino-N-Heterocyclic carbene and ligand transfer to Palladium (II) and rhodium (I)," Dalton Trans., pp. 2917-2922, 2003.

Douthwaite, Richard E. et al., "Cationic and neutral palladium (II) methyl complexes of di-N-Heterocyclic carbenes", J. Chem. Soc., Dalton Trans., pp. 1386-1390, 2002.

Danopoulos, Andreas A. et al., "C-H activation with N-heterocyclic carbene complexes of iridium and rhodium", J. Chem. Soc., Dalton Trans., pp. 3090-3091, 2002.

Yam, Vivian Wing-Wah et al., Unprecedented luminescence behaviour and structural Characterization of a novel class of ruthenium (II) 2,2'- bipyridine complexes with orthometallated aminocarbene ligands, Chem. Commun., pp. 2261-2773, 1998.

Yam, Vivian Wing-Wah et al., "Synthesis, structure, luminescence and electrochemical studies of a novel class of ruthenium (II) polypyridine complexes with ortho-metallated aminocarbene ligands", J. Chem. Soc., Dalton Trans., pp. 1911-1919, 2001.

Herrmann, Wolfgang A. et al., "Metal Complexes of Stable Carbenes", Advanced in organometallic Chemistry, vol. 48, pp. 1-69, 2001.

Herrmann, Wolfgang A. et al., "N-Heterocyclische Carbene", Angew. Chem., vol. 109, pp. 2257-2282, 1997.

Bourissou, Didier et al., Stable Carbenes, Chem. Rev., vol. 100, pp. 30-91, 2000.

Scholl, Matthias et al., "Synthesis and Activity of a New Generation of Ruthenium-Based Olefin Metathesis Catalysts Coordinated with 1,3-Dimesityl-4,5-dihydroimidazol-2-ylidene Ligands", Organic Letters, vol. 1, No. 6, pp. 953-956, 1999.

Boehm, Volker P. W. et al., "Eine Nickel-katalysierte Kreuzkupplung von Arylchloriden mit Aryl-Grignard-Reagentien", Angew. Chem., vol. 112, pp. 1672-1674, 2000.

Dieck, Heindirk Tom et al., "Kupfe (I)-diazabutadien-halogenide", Chem. Ber., vol. 104, pp. 92-109, 1971.

Jafarpour, Laleh et al., "A sterically demanding nucleophilic carbene: 1, 3-bis (2,6-diisopropylphenyl)imidazol-2-ylidene). Thermochemistry and catalytic application in olefin metathesis", Journal of Organometallic Chemistry, vol. 606, pp. 49-54, 2000.

Chakrabarty, Manas et al., "On attempted oxidative cyclisation of isomeric N,N'-diphenylphenylenediamines and their N, N'-dimethyl derivatives by palladium (II) acetate and uv light", Synthetic Communications, vol. 30, No. 20, pp. 3651-3668, 2000.

Foley, Timothy J. et al., "Facile Preparation and Photophysics of Near-Infrared Luminescent Lanthanide (III) Monoporphyrinate Complexes", Inorganic Chemistry vol. 42, pp. 5023-5032, 2003.

Lu, Wei et al., "[(C ^N^N) Pt(C≡C)n R] (HC ^N ^N= 6-aryl-2, 2'-bipyridine, n = 1-4, R = aryl, SiMe3) as a new class of light-emitting materials and their applications in electrophosphorescent devices", Chem. Communication, pp. 206-207, 2002.

U.S. Appl. No. 11/720,291, filed May 25, 2007 Egen, et al.

* cited by examiner

US 7,846,763 B2

TRANSITION METAL COMPLEXES COMPRISING CARBENE LIGANDS SERVING AS EMITTERS FOR ORGANIC LIGHT-EMITTING DIODES (OLED'S)

This application is a 371 of PCT/EP04/09269 filed Aug. 18, 2004.

The present invention relates to the use of transition metal complexes comprising at least one carbene ligand in organic light-emitting diodes (OLEDs), a light-emitting layer, blocking layer for electrons or excitons or blocking layer for holes comprising these transition metal complexes, OLEDs comprising these transition metal complexes, devices comprising an OLED according to the present invention and also specific transition metal complexes comprising at least two carbene ligands.

In organic light-emitting diodes (OLEDs), use is made of the ability of materials to emit light when they are excited by an electric current. OLEDs are of particular interest as alternatives to cathode ray tubes and liquid crystal displays for producing flat VDUs. Owing to their very compact construction and the intrinsically low power consumption, devices comprising OLEDs are particularly useful for mobile applications, for example for use in mobile telephones, laptops, etc.

Numerous materials which emit light on excitation by an electric current have been proposed.

WO 02/15645 relates to OLEDs having a light-emitting layer which comprises phosphorescent transition metal compounds. The transition metal compounds display electrophosporesence, especially in the blue region of the visible electromagnetic spectrum. However, the color coordinates of the blue emitted by the complexes disclosed in WO 02/15645 are in need of improvement.

WO 01/41512 relates to OLEDs having a light-emitting layer which comprises a molecule of the formula $L_2MX$, where M is particularly preferably iridium and L is selected from the group consisting of 2-(1-naphthyl)benzoxazole, 2-phenylbenzoxazole, 2-phenylbenzothiazole, 7,8-benzoquinoline, coumarin, thienylpyridine, phenylpyridine, benzothienylpyridine, 3-methoxy-2-phenylpyridine and tolylpyridine and X is selected from the group consisting of acetylacetonate, hexafluoroacetylacetonate, salicylidene, picolinate and 8-hydroxyquinolinate.

WO 00/70655 relates to electroluminescent layers having a phosphorescent organometallic iridium compound or osmium compound as light-emitting substance. Preference is given to tris(2-phenylpyridine)iridium as light-emitting compound.

Although compounds which display electroluminescence in the blue, red and green regions of the electromagnetic spectrum are already known, the provision of more efficient compounds which can be used industrially is desirable. For the purposes of the present invention, the term electroluminescence refers to both electrofluorescence and electrophosphorescence. Furthermore, the provision of further compounds for use as materials which block electrons, excitons or holes is of interest.

It is an object of the present invention to provide a class of compounds which are suitable for producing electroluminescence in the blue, red and green regions of the electromagnetic spectrum, thus making the production of full-color displays possible. A further object of the present invention is to provide compounds for use as materials which block electrons, excitons or holes.

Figure 1:
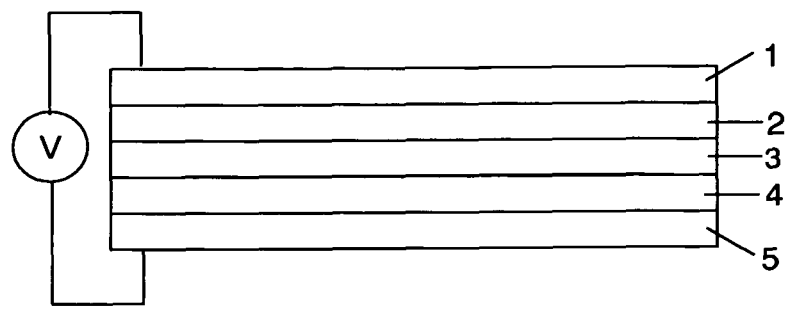
FIG. 1 shows an organic light-emitting diode made up of a plurality of layers.

We have found that these objects are achieved by the use of uncharged transition metal complexes of the formula I comprising at least one carbene ligand in organic light-emitting diodes (OLEDs)

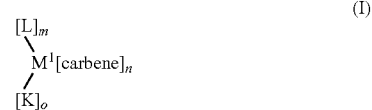

where the symbols have the following meanings:

$M^1$ is a metal atom selected from the group consisting of Co, Rh, Ir, Nb, Pd, Pt, Fe, Ru, Os, Cr, Mo, W, Mn, Tc, Re, Cu, Ag and Au in any oxidation state possible for the respective metal atom;

carbene is a carbene ligand which may be uncharged or monoanionic and monodentate, bidentate or tridentate, with the carbene ligand also being able to be a biscarbene or triscarbene ligand;

L is a monoanionic or dianionic ligand, preferably a monoanionic ligand, which may be monodentate or bidentate;

K is an uncharged monodentate or bidentate ligand selected from the group consisting of phosphines, preferably trialkylphosphines, triarylphosphines or alkylarylphosphines, particularly preferably $PAr_3$, where Ar is a substituted or unsubstituted aryl radical and the three aryl radicals in $PAr_3$ may be identical or different, particularly preferably $PPh_3$, $PEt_3$, $PnBu_3$, $PEt_2Ph$, $PMe_2Ph$, $PnBu_2Ph$; phosphonates and derivatives thereof, arsenates and derivatives thereof, phosphites, CO; pyridines which may be substituted by alkyl or aryl groups; nitriles and dienes which form a π complex with $M^1$, preferably $\eta^4$-diphenyl-1,3-butadiene, $\eta^4$-1,3-pentadiene, $\eta^4$-1-phenyl-1,3-pentadiene, $\eta^4$-1,4-dibenzyl-1,3-butadiene, $\eta^4$-2,4-hexadiene, $\eta^4$-3-methyl-1,3-pentadiene, $\eta^4$-1,4-ditolyl-1,3-butadiene, $\eta^4$-1,4-bis(trimethylsilyl)-1,3-butadiene and $\eta^2$- or $\eta^4$-cyclooctadiene (each 1,3 and 1,5), particularly preferably 1,4-diphenyl-1,3-butadiene, 1-phenyl-1,3-pentadiene, 2,4-hexadiene, butadiene, $\eta^2$-cyclooctene, $\eta^4$-1,3-cyclooctadiene and $\eta^4$-1,5-cyclooctadiene;

n is the number of carbene ligands, where n is at least 1 and when n>1 the carbene ligands in the complex of the formula I can be identical or different;

m is the number of ligands L, where m can be 0 or ≧1 and when m>1 the ligands L can be identical or different;

o is the number of ligands K, where o can be 0 or ≧1 and when o>1 the ligands K can be identical or different;

where the sum n+m+o is dependent on the oxidation state and coordination number of the metal atom and on the denticity of the ligands carbene, L and K and also on the charge on the ligands carbene and L, with the proviso that n is at least 1.

The transition metal complexes of the formula I can be used in any layer of an OLED, with the ligand skeleton or central metal being able to be varied to match it to desired properties of the metal complexes. For example, the transition metal complexes of the formula I can be used in a blocking layer for electrons, a blocking layer for excitons, a blocking layer for holes or the light-emitting layer of the OLED. The compounds of the formula I are preferably used as emitter molecules in OLEDs.

For the purposes of the present invention, a bidentate ligand is a ligand which is coordinated at two points to the transition metal atom $M^1$.

For the purposes of the present invention a monodentate ligand is a ligand which coordinates at one point of the ligand to the transition metal atom $M^1$.

Depending on the coordination number of the metal $M^1$ used and the nature and number of the ligands L, K and carbene used, various isomers of the corresponding metal complexes can be present for the same metal $M^1$ and the same nature and number of the ligands K, L and carbene used. For example, in the case of complexes of a metal $M^1$ which have the coordination number 6 (i.e. octahedral complexes), for example Ir(III) complexes, both cis/trans isomers are possible when the complexes have the general composition $MA_2B_4$, and fac/mer isomers (facial/meridional isomers) are possible when the complexes have the general composition $MA_3B_3$. In the case of square planar complexes of a metal $M^1$ which have the coordination number 4, for example Pt(II) complexes, cis/trans isomers are possible when the complexes have the general composition $MA_2B_2$. The symbols A and B are each a binding point of a ligand, with not only monodentate but also bidentate ligands being able to be present. An unsymmetrical bidentate ligand has, according to the abovementioned general composition, one group A and one group B.

A person skilled in the art will know what is meant by cis/trans or fac/mer isomers. In the case of octahedral complexes, the cis isomer is present in the case of complexes of the composition $MA_2B_4$ when the two groups A occupy adjacent corners of an octahedron, while the two groups A of the trans isomer occupy opposite corners of an octahedron. In the case of complexes of the composition $MA_3B_3$, three groups of the same type can occupy either the corners of one face of the octahedron (facial isomer) or a meridian, i.e. two of the three ligand bonding points are in trans positions relative to one another (meridional isomer). For the definition of cis/trans isomers and fac/mer isomers in octahedron metal complexes see, for example, J. Huheey, E. Keiter, R, Keiter, Anorganische Chemie: Prinzipien von Struktur und Reaktivität, 2nd, revised edition, translated and expanded by Ralf Steudel, Berlin; N.Y.: de Gruyter, 1995, pages 575, 576.

In the case of square planar complexes, the cis isomer is present in the case of complexes of the composition $MA_2B_2$ when both the two groups A and the two groups B occupy adjacent corners of a square, while in the trans isomer both the two groups A and the two groups B in each case occupy the two diagonally opposite corners of a square. For the definition of cis/trans isomers in square planar metal complexes, see, for example, J. Huheey, E. Keiter, R, Keiter, Anorganische Chemie: Prinzipien von Struktur und Reaktivität, 2nd, revised edition, translated and expanded by Ralf Stendel, Berlin; N.Y.: de Gruyter, 1995, pages 557 to 559.

In general, the various isomers of the metal complexes of the formula I can be separated by methods known to those skilled in the art, for example by chromatography, sublimation or crystallization.

The present invention thus relates both to individual isomers of the transition metal complexes of the formula I and to mixtures of various isomeres in any mixing ratio.

Transition metal complexes which comprise carbene ligands are known from the prior art. Thus, Gründemann et al., J. Am. Chem. Soc., 2002, 124, 10473 to 10481 and Danapoulos et al., J. Chem. Soc., Dalton Trans., 2002, 3090 to 3091, describe iridium complexes which have a carbene ligand comprising the following structural unit

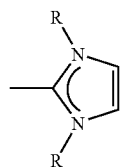

Hitchcock et al. J. Organomet. Chem., 1982, 239, C 26-C 30, disclose iridium(III) complexes which have three monoanionic carbene ligands and possess the following structural formula

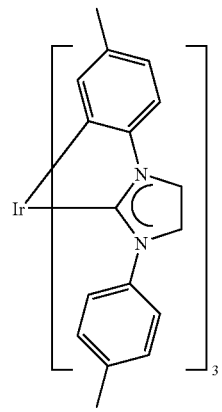

However, none of the documents mentioned disclose luminescence properties, in particular electroluminescence properties, of the compounds disclosed or their use in OLEDs.

Yam et al., Chem. Commun. 1989, 2261 to 2262 and Yam et al., J. Chem. Soc. Dalton Trans., 2001, 1911 to 1919, disclose ruthenium complexes which have a carbene ligand. The photophysical properties of these carbene complexes, including the photoluminescence of the complexes, was examined in the documents cited. However, nothing is said about use of these complexes, nor do the documents give information regarding the electroluminescence of the compounds studied.

Che et al., Organometallics 1998, 17, 1622 to 1630, describe cationic Re complexes having a carbene ligand comprising the following structural unit

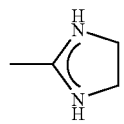

This complex displays photoluminescence. However, a use of the Re complex or a study of the electroluminescence behavior of the complex is not disclosed.

U.S. Pat. No. 6,160,267 and U.S. Pat. No. 6,338,977 relate to a molecular light-emitting diode whose color changes as a function of the vapors surrounding it. This electrode has a sensor-emitter layer comprising an uncharged platinum complex in which platinum is complexed by two negatively charged ligands selected from the group consisting of CN⁻, NO₂⁻, NCO⁻, NCS⁻, Cl⁻, Br⁻, I⁻ and oxalate and the further two ligands are selected from among at least one and at most two aryl isonitrile groups and a Fischer carbene complex having the formula =C(Y)—NH—C₆H₄-alkyl, where Y is O-alkyl, NH-alkyl or N(alkyl)₂. A necessary feature of the Pt complexes disclosed in U.S. Pat. No. 6,160,267 and U.S. Pat. No. 6,338,977 is the presence of at least one aryl isonitrile group.

The suitability of transition metal complexes of the formula I according to the present invention which bear at least one carbene ligand as light-emitting substances in OLEDs, with the substances of this structural type corresponding to the formula I being suitable for electroluminescence in the red, green and blue regions of the electromagnetic spectrum, is mentioned in none of the abovementioned documents.

It has thus been found that the transition metal complexes of the formula I as set forth in the present patent application are suitable as light-emitting substances in OLEDs for producing full-color displays.

The transition metal complexes of the formula I used according to the present invention particularly preferably have a metal atom $M^1$ selected from the group consisting of Os, Rh, Ir, Ru, Pd and Pt, with preference being given to Os(IV), Rh(III), Ir(I), Ir(III), Ru(III), Ru(IV), Pd(III) and Pt(II). Metal atoms which are particularly preferably used are Ru, Rh, Ir and Pt, preferably Ru(III), Ru(IV), Rh(III), Ir(I), Ir(III) and Pt(II). Very particular preference is given to using Ir or Pt, preferably Ir(III) or Pt(II), very particularly preferably Ir(III), as metal atom $M^1$.

Suitable monoanionic or dianionic ligands L, preferably monoanionic ligands L, which may be monodentate or bidentate are the ligands customarily used as monodentate or bidentate monoanionic or dianionic ligands.

Suitable monoanionic monodentate ligands are, for example, halides, in particular Cl⁻ and Br⁻, pseudohalides, in particular CN⁻, cyclopentadienyl (Cp⁻), alkyl radicals which are linked to the transition metal $M^1$ via a sigma bond, for example CH₃, alkylaryl radicals which are linked to the transition metal $M^1$ via a sigma bond, for example benzyl.

Suitable monoanionic bidentate ligands are, for example, acetylacetonate and its derivatives, picolinate, Schiff bases, amino acids and the bidentate monoanionic ligands mentioned in WO 02/15645, with acetylacetonate and picolinate being preferred.

Suitable uncharged monodentate or bidentate ligands have been mentioned above. Preferred uncharged monodentate ligands are selected from the group consisting of PPh₃, P(OPh)₃, AsPh₃, CO, pyridine, nitriles and their derivatives. Particularly preferred uncharged monodentate or bidentate ligands are 1,4-diphenyl-1,3-butadiene, 1-phenyl-1,3-pentadiene, 2,4-hexadiene, $\eta^4$-cyclooctadiene and $\eta^2$-cyclooctadiene (each 1,3 or 1,5).

The number n of the carbene ligands in uncharged transition metal complexes in which the transition metal atom Ir(III) has a coordination number of 6 is from 1 to 3, preferably 2 or 3, particularly preferably 3. If n>1, the carbene ligands can be identical or different, but are preferably identical.

The number n of the carbene ligands in transition metal complexes in which the transition metal atom Pt(II) has a coordination number of 4 is 1 or 2, preferably 2. If n is >1, the carbene ligands can be identical or different.

The number m of monoanionic ligands L in the abovementioned case is from 0 to 2, preferably 0 or 1, particularly preferably 0. If m>1, the ligands L can be identical or different, but are preferably identical.

The number o of uncharged ligands K is dependent on whether the coordination number 6 of the Ir(III) or 4 of the Pt(II) has been reached by the total of carbene ligands and the ligands L. If, in the case where Ir(III) is used, n is three and three monoanionic bidentate carbene ligands are used, then o in the abovementioned case is 0. If, when Pt(II) is used, n is two and two monoanionic bidentate carbene ligands are used, then o is in this case likewise 0.

In one embodiment, the present invention provides for the use of transition metal complexes of the formula IA

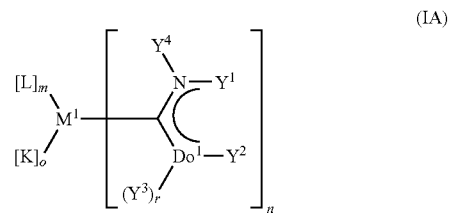

where the symbols have the following meanings:

$Do^1$ is a donor atom selected from the group consisting of C, N, O, P and S, preferably N, O, P and S, particularly preferably N;

r is 2, when $Do^1$ is C, is 1, when $Do^1$ is N or P and is 0 when $Do^1$ is O or S;

$Y^1$, $Y^2$ are each, independently of one another, hydrogen or a carbon-containing group selected from the group consisting of alkyl, aryl, heteroaryl and alkenyl groups, preferably alkyl and aryl groups, or $Y^1$ and $Y^2$ together form a bridge between the donor atom $Do^1$ and the nitrogen atom N which has at least two atoms, preferably two or three atoms, particularly preferably two atoms, of which at least one is a carbon atom and the further atoms are preferably nitrogen or carbon atoms, where the bridge may be saturated or unsaturated, preferably unsaturated, and the two or more atoms of the bridge can be substituted or unsubstituted;

$Y^3$, $Y^4$ are each, independently of one another, a hydrogen, alkyl, aryl, heteroaryl or alkenyl radical; preferably hydrogen or an alkyl, heteroaryl or aryl radical, where $Y^1$, $Y^2$, $Y^3$ and $Y^4$ must not all at the same time be hydrogen.

The symbols $M^1$, L, K and n, m and o have been mentioned above.

In the case of the groups Y1 and Y2, the following applies for the purposes of the present patent application:

the substituents of the groups $Y^1$ and $Y^2$ can together form a bridge having a total of from three to five, preferably four, atoms of which one or two atoms may be heteroatoms, preferably N, and the remaining atoms are carbon atoms, so that $Y^1$ and $Y^2$ together with this bridge form a five- to seven-membered, preferably six-membered, ring which may, if appropriate, have two or, in the case of a six- or seven-membered ring, three double bonds and may, if appropriate, be substituted by alkyl or aryl groups and may, if appropriate, comprise heteroatoms, preferably N, with a six-membered aromatic ring which is substituted by alkyl or aryl groups or unsubstituted being preferred, or the preferred six-membered aromatic ring is fused with further rings, preferably six-membered aromatic rings, which may, if appropriate, comprise at least one heteroatom, preferably N.

For the purposes of the present patent application, the terms aryl radical or group, heteroaryl radical or group, alkyl radical or group and alkenyl radical or group have the following meanings:

An aryl radical (or group) is a radical which has a basic skeleton containing from 6 to 30 carbon atoms, preferably from 6 to 18 carbon atoms, and is made up of an aromatic ring or a plurality of fused aromatic rings. Suitable basic skeletons are, for example, phenyl, naphthyl, anthracenyl or phenanthrenyl. This basic skeleton can be unsubstituted (i.e. all carbon atoms which are able to be substituted bear hydrogen atoms) or be substituted on one, more than one or all positions capable of being substituted in the basic skeleton. Suitable substituents are, for example, alkyl radicals, preferably alkyl radicals having from 1 to 8 carbon atoms, particularly preferably methyl, ethyl or i-propyl, aryl radicals, preferably $C_6$-aryl radicals, which may in turn be substituted or unsubstituted, heteroaryl radicals, preferably heteroaryl radicals comprising at least one nitrogen atom, particularly preferably pyridyl radicals, alkenyl radicals, preferably alkenyl radicals containing one double bond, particularly preferably alkenyl radicals having one double bond and from 1 to 8 carbon atoms, or groups which act as donors or acceptors. Donor groups are groups which have a +I and/or +M effect, and acceptor groups are groups which have a −I and/or −M effect. Suitable groups which act as donors or acceptors are halogen radicals, preferably F, Cl, Br, particularly preferably F, alkoxy radicals, aryloxy radicals, carbonyl radicals, ester radicals, amine radicals, amide radicals, $CH_2F$ groups, $CHF_2$ groups, $CF_3$ groups, CN groups, thio groups or SCN groups. The aryl radicals very particularly preferably bear substituents selected from the group consisting of methyl, F, Cl, aryloxy and alkoxy. The aryl radical or the aryl group is preferably a $C_6$-$C_{18}$-aryl radical, particularly preferably a $C_6$-aryl radical which is optionally substituted by one or more of the abovementioned substituents. The $C_6$-$C_{18}$-aryl radical, preferably $C_6$-aryl radical, particularly preferably bears one or two of the abovementioned substituents, with, in the case of a $C_6$-aryl radical, one substituent being located in the ortho, meta or para position relative to the further linkage point of the aryl radical and, in the case of two substituents, these can be located in the meta position or ortho position relative to the further linkage point of the aryl radical or one radical is located in the ortho position and one radical is located in the meta position or one radical is located in the ortho or meta position and the further radical is located in the para position.

A heteroaryl radical or a heteroaryl group is a radical which differs from the abovementioned aryl radicals in that at least one carbon atom in the basic skeleton of the aryl radical is replaced by a heteroatom. Preferred heteroatoms are N, O and S. Very particular preference is given to one or two carbon atoms of the basic skeleton of the aryl radicals being replaced by heteroatoms. In particular, the basic skeleton is selected from among electron-rich systems such as pyridyl and five-membered heteroaromatics such as pyrrole, furans. The basic skeleton can be substituted at one, more than one or all positions of the basic skeleton which are capable of being substituted. Suitable substituents are the same ones as those mentioned above for the aryl groups.

An alkyl radical or an alkyl group is a radical having from 1 to 20 carbon atoms, preferably from 1 to 10 carbon atoms, particularly preferably from 1 to 8 carbon atoms. This alkyl radical can be branched or unbranched and may, if appropriate, be interrupted by one or more heteroatoms, preferably Si, N, O or S, particularly preferably N, O or S. Furthermore, this alkyl radical can be substituted by one or more of the substituents mentioned for the aryl groups. It is likewise possible for the alkyl radical to bear one or more aryl groups. In this case, all of the abovementioned aryl groups are suitable. The alkyl radicals are particularly preferably selected from the group consisting of methyl and of isopropyl.

An alkenyl radical or an alkenyl group is a radical which corresponds to the abovementioned alkyl radicals having at least two carbon atoms, with the difference that at least one C—C single bond of the alkyl radical is replaced by a C=C double bond. The alkenyl radical preferably has one or two double bonds.

A bridge having at least two atoms of which at least one is a carbon atom and the further atoms are preferably nitrogen or carbon atoms, where the bridge can be saturated or preferably unsaturated and the two or more atoms of the bridge may be substituted or unsubstituted, is preferably one of the following groups:

A bridge having two carbon atoms or one carbon atom and one nitrogen atom, where the carbon atoms or a carbon atom and a nitrogen atom are joined by means of a double bond so that the bridge has one of the following formulae, with the bridge preferably having two carbon atoms:

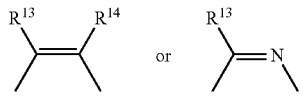

$R^{13}$ and $R^{14}$ are each, independently of one another, hydrogen, alkyl or aryl or $R^{13}$ and $R^{14}$ together form a bridge having a total of from 3 to 5, preferably 4, atoms of which one or two atoms may, if appropriate, be heteroatoms, preferably N, and the remaining atoms are carbon atoms, so that this group forms a 5- to 7-membered, preferably 6-membered, ring which may, if appropriate, contain, in addition to the existing double bond, one further double bond, or in the case of a 6- or 7-membered ring two further double bonds, and may optionally be substituted by alkyl or aryl groups. Preference is in this case given to a six-membered aromatic ring. This may be substituted by alkyl or aryl groups or be unsubstituted. Furthermore, it is possible for one or more further aromatic rings to be fused onto this, preferably six-membered, aromatic ring. In this case, any conceivable fusion is possible. These fused-on radicals may in turn be substituted, preferably by the radicals mentioned in the general definition of the aryl radicals.

A bridge having two carbon atoms joined to one another by means of a single bond, so that the bridge has the following formula:

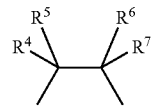

where $R^4$,
$R^5$, $R^6$
and $R^7$ are each, independently of one another, hydrogen, alkyl, aryl, heteroaryl or alkenyl, preferably hydrogen, alkyl or aryl.

$M^1$ in the transition metal complex of the formula IA is very particularly preferably Ir(III).

The group

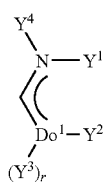

is very particularly preferably selected from the group consisting of

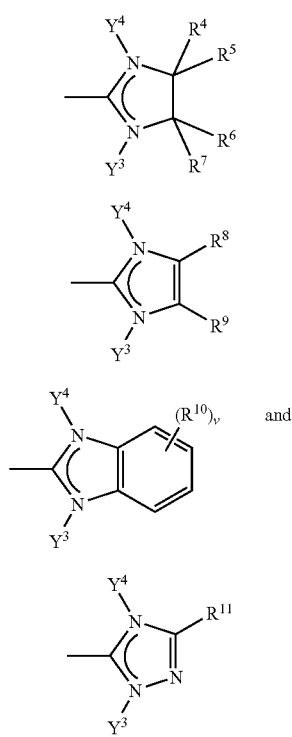

where the symbols have the following meanings:
$R^4$, $R^5$, $R^6$,
$R^7$, $R^8$, $R^9$
and $R^{11}$ are each hydrogen, alkyl, aryl, heteroaryl, alkenyl or a substituent which acts as a donor or acceptor and is preferably selected from among halogen radicals, preferably F, Cl, Br, particularly preferably F, alkoxy radicals, aryloxy radicals, carbonyl radicals, ester radicals, amine radicals, amide radicals, $CH_2F$ groups, $CHF_2$ groups, $CF_3$ groups, CN groups, thio groups and SCN groups;
$R^{10}$ is alkyl, aryl, heteroaryl, alkenyl, preferably alkyl, heteroaryl or aryl, or 2 radicals $R^{10}$ together form a fused-on ring which may, if appropriate, comprise one or more heteroatoms, preferably N, preferably form a fused-on aromatic $C_6$ ring, where one or more further aromatic rings may, if appropriate, be fused on to this, preferably six-membered, aromatic ring in any conceivable fashion and the fused-on radicals may in turn be substituted; or $R^{10}$ is a radical which acts as a donor or acceptor, preferably selected from among halogen radicals, preferably F, Cl, Br, particularly preferably F; alkoxy, aryloxy, carbonyl, ester, amino groups, amide radicals, $CHF_2$, $CH_2F$, $CF_3$, CN, thio groups and SCN;
v is from 0 to 4, preferably 0, 1 or 2, very particularly preferably 0, where, when v is 0, all 4 possible substituents on the aryl radical in formula c are hydrogen atoms.
The radicals $Y^3$ and $Y^4$ have been defined above.

In a further, preferred embodiment of the present invention, the carbene ligand or ligands in the uncharged transition metal complexes of the formula I is/are each a bidentate and/or monoanionic carbene ligand. The carbene ligand is very particularly preferably a monoanionic bidentate carbene ligand.

The carbene ligand or ligands in the uncharged transition metal complex of the formula I very particularly preferably has/have the formula (II)

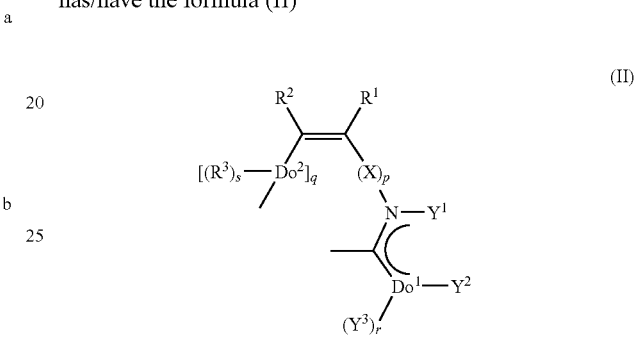

(II)

where the symbols have the following meanings:
$Do^1$ is a donor atom selected from the group consisting of C, P, N, O and S, preferably P, N, O and S, particularly preferably N;
$Do^2$ is a donor atom selected from the group consisting of C, N, P, O and S;
r is 2, when $Do^1$ is C, is 1 when $Do^1$ is N or P and is 0 when $Do^1$ is O or S;
s is 2 when $Do^2$ is C, is 1 when $Do^2$ is N or P and is 0 when $Do^2$ is O or S;
X is a spacer selected from the group consisting of silylene, alkylene, arylene, heteroarylene and alkenylene, preferably alkylene or arylene, particularly preferably $C_1$-$C_3$-alkylene or $C_6$-1,4-arylene, where at least one of the four further carbon atoms may optionally be substituted by methyl, ethyl, n-propyl or i-propyl groups or by groups which act as donors or acceptors selected from among halogen radicals, preferably F, Cl, Br, particularly preferably F, alkoxy radicals, aryloxy radicals, carbonyl, ester, amino groups, amide radicals, $CHF_2$, $CH_2F$, $CF_3$, CN, thio groups and SCN; very particularly preferably methylene, ethylene or 1,4-phenylene;
p is 0 or 1, preferably 0;
q is 0 or 1, preferably 0;
$Y^1$, $Y^2$ are each, independently of one another, hydrogen or a carbon-containing group selected from the group consisting of alkyl, aryl, heteroaryl and alkenyl groups; preferably alkyl, heteroaryl and aryl groups; or
$Y^1$ and $Y^2$ together form a bridge between the donor atom $Do^1$ and the nitrogen atom N which has at least two atoms, preferably two or three atoms, particularly preferably two atoms, of which at least one is a carbon atom and the further atom or atoms is/are each a nitrogen atom, where the bridge may be saturated or unsaturated, preferably unsaturated, and the two or more atoms of the bridge may be substituted or unsubstituted;

$Y^3$ is hydrogen or an alkyl, aryl, heteroaryl or alkenyl radical, preferably hydrogen or an alkyl, heteroaryl or an aryl radical, or

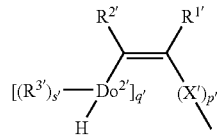

where $Do^{2'}$, $q'$, $s'$, $R^{3'}$, $R^{1'}$, $R^{2'}$, $X'$ and $p'$ are each, independently of one another, as defined for $Do^2$, $q$, $s$, $R^3$, $R^1$, $R^2$, $X$ and $p$;

$R^1$, $R^2$ are each, independently of one another, hydrogen or an alkyl, aryl, heteroaryl or alkenyl radical, preferably hydrogen, an alkyl radical, a heteroaryl radical or an aryl radical; or $R^1$ and $R^2$ together form a bridge having a total of from three to five, preferably four, atoms of which one or two atoms may be heteroatoms, preferably N, and the remaining atoms are carbon atoms, so that the group

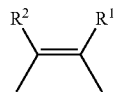

forms a five- to seven-membered, preferably six-membered, ring which may, if appropriate, contain, in addition to the existing double bond, one further double bond or in the case of a six- or seven-membered ring two further double bonds and may optionally be substituted by alkyl or aryl groups and may, if appropriate, comprise heteroatoms, preferably N, with a six-membered aromatic ring which is substituted by alkyl or aryl groups or is unsubstituted being preferred, or the preferred six-membered aromatic ring is fused with further rings which may, if appropriate, comprise at least one heteroatom, preferably N, preferably six-membered aromatic rings;

$R^3$ is hydrogen or an alkyl, aryl, heteroaryl or alkenyl radical, preferably hydrogen or an alkyl, heteroaryl or aryl radical.

Preference is given to ligands of the formula II in which p and/or q are 0, i.e. there are no spacers X and/or no donor atoms $Do^2$ present in the ligands of the formula II.

The group

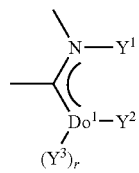

is preferably selected from the group consisting of

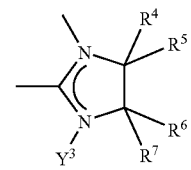
a

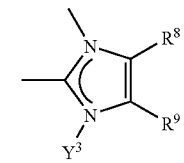
b

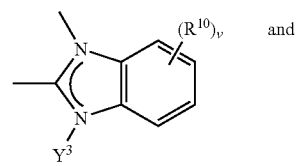
and
c

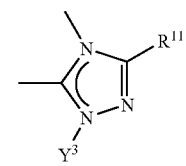
d where the symbols have the following meanings:
$R^4$, $R^5$, $R^6$,
$R^7$, $R^8$, $R^9$
and $R^{11}$ are each hydrogen, alkyl, aryl, heteroaryl, alkenyl or a substituent which acts as a donor or acceptor and is preferably selected from among halogen radicals, preferably F, Cl, Br, particularly preferably F, alkoxy radicals, aryloxy radicals, carbonyl radicals, ester radicals, amine radicals, amide radicals, $CH_2F$ groups, $CHF_2$ groups, $CF_3$ groups, CN groups, thio groups and SCN groups, preferably hydrogen, alkyl, heteroaryl or aryl;

$R^{10}$ is alkyl, aryl, heteroaryl, alkenyl, preferably alkyl or aryl, or 2 radicals $R^{10}$ together form a fused-on ring which may, if appropriate, comprise one or more heteroatoms, preferably N, preferably form a fused-on aromatic $C_6$ ring, where one or more further aromatic rings may, if appropriate, be fused on to this, preferably six-membered, aromatic ring in any conceivable fashion and the fused-on radicals may in turn be substituted; or $R^{10}$ is a radical which acts as a donor or acceptor, preferably selected from among halogen radicals, preferably F, Cl, Br, particularly preferably F; alkoxy, aryloxy, carbonyl, ester, amino groups, amide radicals, $CHF_2$, $CH_2F$, $CF_3$, CN, thio groups and SCN;

V is from 0 to 4, preferably 0, 1 or 2, very particularly preferably 0, where, when v is 0, all 4 possible carbon atoms on the aryl radical in formula c which are optionally substituted by $R^{10}$ bear hydrogen atoms;

$Y^3$ has been defined above.

The group

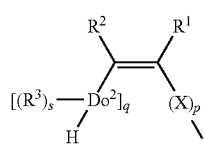

of the carbene ligand of the formula II is preferably

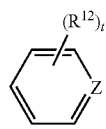

where the symbols have the following meanings:
Z is CH or N and can be located in the o, m or p position relative to the point of linkage of the group to the carbene ligand;
$R^{12}$ is an alkyl, aryl, heteroaryl or alkenyl radical, preferably an alkyl or aryl radical, or 2 radicals $R^{12}$ together form a fused-on ring which may, if appropriate, comprise one or more heteroatoms, preferably N, preferably form a fused-on aromatic $C_6$ ring, where one or more further aromatic rings may, if appropriate, be fused onto this, preferably six-membered, aromatic ring in any conceivable fashion, and the fused-on radicals may in turn be substituted; or $R^{12}$ is a radical which acts as a donor or acceptor, preferably selected from the group consisting of halogen radicals, preferably F, Cl, Br, particularly preferably F; alkoxy, aryloxy, carbonyl, ester, amino groups, amide radicals, $CHF_2$, $CH_2F$, $CF_3$, CN, thio groups and SCN;
t is 0 to 3 and when t>1 the radicals $R^{12}$ can be identical or different; t is preferably 0 or 1 and when t is 1 the radical $R^{12}$ is located in the ortho, meta or para position relative to the point of linkage to the spacer X or, when p is 0, to the point of linkage to the nitrogen atom adjacent to the carbene carbon.

In the carbene ligands of the formula II, $Y^3$ can be identical to or different from the above-defined group and have one of the following meanings which have been mentioned above;
a hydrogen atom or an alkyl, aryl, heteroaryl or alkenyl radical, preferably a hydrogen atom or an alkyl, heteroaryl or aryl radical or

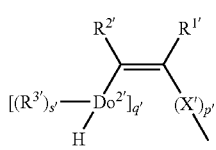

where $Do^{2'}$, q', s', $R^{3'}$, $R^{1'}$, $R^{2'}$, X' and p' are each, independently of one another, defined as for $Do^2$, q, s, $R^3$, $R^1$, $R^2$, X and p.

Apart from carbene ligands of the formula II in which $Y^4$, i.e. the group of formula

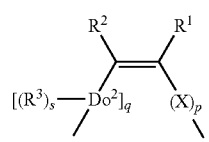

is the structure

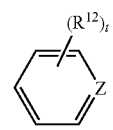

and $Y^3$ is

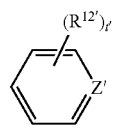

carbene ligands in which $Y^4$, i.e. the group of formula

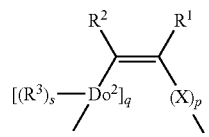

is the structure

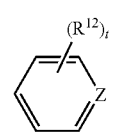

and $Y^3$ is
a hydrogen atom or an alkyl, aryl, heteroaryl or alkenyl radical, preferably a hydrogen atom or an alkyl, heteroaryl or aryl radical, are also suitable.

The definitions of the symbols correspond to the definitions given above.

The carbene ligand or ligands of the formula II is/are very particularly preferably selected from the group consisting of

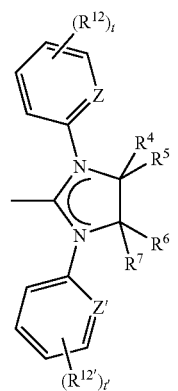

a

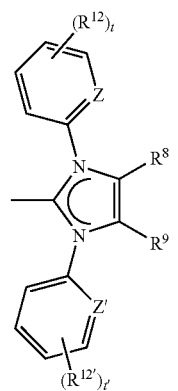

b

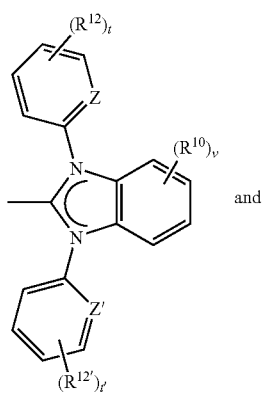

and c

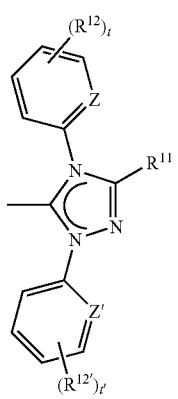

d where the symbols have the following meanings:

Z, Z' are identical or different and are each CH or N;

$R^{12}$, $R^{12'}$ are identical or different and are each an alkyl, aryl, heteroaryl or alkenyl radical, preferably an alkyl or aryl radical, or 2 radicals $R^{12}$ or $R^{12'}$ together form a fused-on ring which may, if appropriate, comprise one or more heteroatoms, preferably N, preferably form a fused-on aromatic $C_6$ ring, where one or more further aromatic rings may, if appropriate, be fused onto this, preferably six-membered, aromatic ring in any conceivable fashion, and the fused-on radicals may in turn be substituted; or $R^{12}$ or $R^{12'}$ is a radical which acts as a donor or acceptor, preferably selected from the group consisting of halogen radicals, preferably F, Cl, Br, particularly preferably F; alkoxy, aryloxy, carbonyl, ester, amino groups, amide radicals, $CHF_2$, $CH_2F$, $CF_3$, CN, thio groups and SCN;

t and t' are identical or different, preferably identical, and are each 0 to 3 and when t or t'>1 the radicals $R^{12}$ or $R^{12'}$ can be identical or different; t or t' is preferably 0 or 1 and when t or t' is 1 the radical $R^{12}$ or $R^{12'}$ is located in the ortho, meta or para position relative to the point of linkage to the nitrogen atom adjacent to the carbene carbon;

$R^4$, $R^5$, $R^6$, $R^7$, $R^8$, $R^9$ and $R^{11}$ are each hydrogen, alkyl, aryl, heteroaryl, alkenyl or a substituent which acts as a donor or acceptor and is preferably selected from among halogen radicals, preferably F, Cl, Br, particularly preferably F, alkoxy radicals, aryloxy radicals, carbonyl radicals, ester radicals, amine radicals, amide radicals, $CH_2F$ groups, $CHF_2$ groups, $CF_3$ groups, CN groups, thio groups and SCN groups, preferably hydrogen, alkyl, heteroaryl or aryl;

$R^{10}$ is alkyl, aryl, heteroaryl, alkenyl, preferably alkyl, heteroaryl or aryl, or 2 radicals $R^{10}$ together form a fused-on ring which may, if appropriate, comprise one or more heteroatoms, preferably N, preferably form a fused-on aromatic $C_6$ ring, where one or more further aromatic rings may, if appropriate, be fused on to this, preferably six-membered, aromatic ring in any conceivable fashion and the fused-on radicals may in turn be substituted; or $R^{10}$ is a radical which acts as a donor or acceptor, preferably selected from among halogen radicals, preferably F, Cl, Br, particularly preferably F; alkoxy, aryloxy, carbonyl, ester, amino groups, amide radicals, $CHF_2$, $CH_2F$, $CF_3$, CN, thio groups and SCN;

v is from 0 to 4, preferably 0, 1 or 2, very particularly preferably 0, where, when v is 0, all 4 possible carbon atoms on the aryl radical in formula c which are optionally substituted by $R^{10}$ bear hydrogen atoms.

Preferred transition metal complexes of the formula (I) are thus ones which comprise at least one carbene ligand of the formula II, with preferred embodiments of the carbene ligand of the formula II having been mentioned above.

Particularly preferred transition metal complexes of the formula I are thus ones which have the formula I(B)

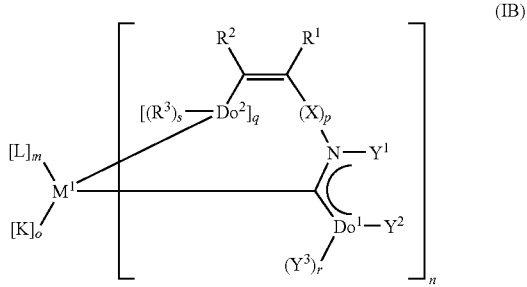

(IB)

The meanings of the symbols correspond to the meanings indicated above in respect of the transition metal complex (I) and in respect of the carbene ligand (II). Preferred embodiments have likewise been mentioned above.

The transition metal complexes of the formula IB can, if a metal atom $M^1$ having the coordination number 6 is used, be present as facial or meridional isomer or as an isomer mixture of facial and meridional isomers in any ratios when they have a composition $MA_3B_3$, as indicated above. Depending on the properties of the facial or meridional isomer of the transition metal complexes of the formula IB, preference can be given to using either an isomerically pure facial isomer or an isomerically pure meridional isomer or an isomer mixture of facial and meridional isomers in which one of the isomers is present in excess or the two isomers are present in equal amounts. For example, facial and meridional isomers of the transition metal complex of the formula IB are possible when n is 3 and m and o are 0. When the transition metal complexes of the formula IB have a composition $MA_2B_4$, the transition metal complexes can be present in the form of cis/trans isomers in any ratios, as indicated above. Depending on the properties of the cis or trans isomer of the transition metal complexes of the formula IB, preference can be given to using either an isomerically pure cis isomer or an isomerically pure trans isomer or an isomer mixture of cis and trans isomers in which one of the isomers is present in excess or the two isomers are present in equal amounts. Cis/trans isomers of complexes of the formula IB are possible, for example, when $M^1$ is a metal atom having the coordination number 6 and when n is 2 and m is 2, in which case the two monodentate ligands L are identical, and o is 0 or when o is 2 and the two monodentate ligands K are identical and m is 0.

In the case of uncharged transition metal complexes in which the transition metal atom is Ir(III) having a coordination number of 6, the number of the preferably monoanionic bidentate carbene ligands n is at least 1 and not more than 3. The number of the preferred monoanionic bidentate carbene ligands is preferably 2 or 3, particularly preferably 3. When n>1, the carbene ligands can be identical or different.

The transition metal complexes of the formula IB can, if a metal atom $M^1$ having the coordination number 4 which forms square planar complexes is used, be present as cis or trans isomers or as an isomer mixture of cis and trans isomers in any ratios when they have a composition $MA_2B_2$, as indicated above. For example, cis/trans isomers of the transition metal complexes of the formula IB are possible when n is 2 and m and o are 0.

In the case of uncharged transition metal complexes in which the transition metal atom is Pt(II) having a coordination number of 4, the number n of the preferred monoanionic bidentate carbene ligands n is 1 or 2, preferably 2. When n=2, the carbene ligands can be identical or different.

Very particular preference is given to a transition metal complex in which $M^1$ is Ir(III) having a coordination number of 6. In this Ir(III) complex, very particular preference is given to n being 3, m being 0, o being 0, q being 0, p being 0, $Do^1$ being N and r being 1, with the remaining symbols being as defined above.

Especial preference is given to transition metal complexes of the formulae IBa to d selected from the group consisting of

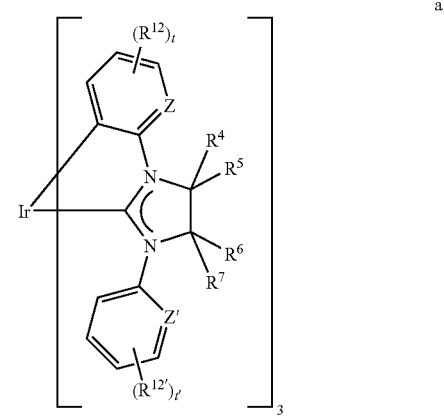

a

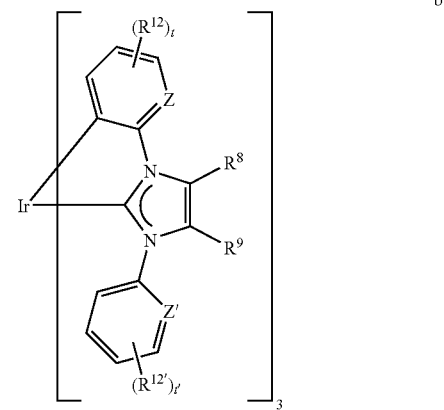

b

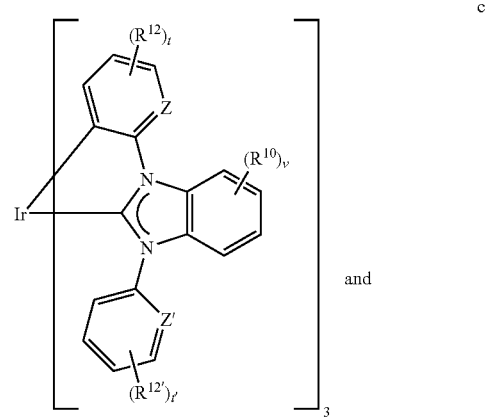

and c

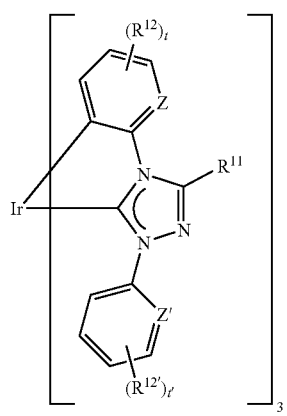

where the symbols have the meanings indicated above in respect of the preferred carbene ligands.

Among these Ir(III) complexes, very particular preference is given to those of the formulae b, c and d. Especial preference is given to Ir(II) complexes in which Z and Z' are each CH, $R^8$ and $R^9$ are each H, t, t' and v are each 0 and the remaining radicals have the meanings indicated above in respect of the preferred carbene ligands.

The abovementioned uncharged transition metal complexes are very useful as emitter molecules in organic light-emitting diodes (OLEDs). Simple variations of the ligands or the central metal make it possible to provide transition metal complexes which display electroluminescence in the red, green or, in particular, blue region of the electromagnetic spectrum. The uncharged transition metal complexes used according to the present invention are therefore suitable for use in industrially usable full-color displays.

Furthermore, the abovementioned uncharged transition metal complexes are suitable as electron blockers, exciton blockers or hole blockers in OLEDs, depending on the ligands used and the central metal used.

The present invention further provides uncharged transition metal complexes of the formula IC

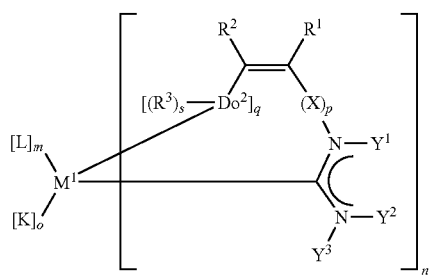

(IC)

where the symbols have the following meanings:
$M^1$ is Ru, Rh, Ir, Pt in any oxidation state possible for the respective metal atom, preferably Ir or Pt;
L is a monoanionic or dianionic ligand, preferably a monoanionic ligand, which may be monodentate or bidentate;
K is an uncharged monodentate or bidentate ligand;
n is the number of carbene ligands, where n is at least 2 and the carbene ligands in the transition metal complex can be identical or different;

m is the number of ligands L, where m can be 0 or $\geq 1$ and when m>1 the ligands L can be identical or different;
o is the number of ligands K, where o can be 0 or $\geq 1$ and in the case of o>1 the ligands K can be identical or different;

where the sum n+m+o is dependent on the oxidation state and coordination number of the metal atom used and the denticity of the ligands and also on the charge on the ligands, with the proviso that n is at least 2;
$Do^2$ is a donor atom selected from the group consisting of C, N, P, O and S;
s is 2 when $Do^2$ is C, is 1 when $Do^2$ is N or P and is 0 when $Do^2$ is O or S;
X is a spacer selected from the group consisting of silylene, alkylene, arylene, heteroarylene and alkenylene, preferably alkylene or arylene, particularly preferably $C_1$-$C_3$-alkylene or $C_6$-1,4-arylene, where at least one of the four further carbon atoms may optionally be substituted by methyl, ethyl, n-propyl or i-propyl groups or by groups which act as donors or acceptors selected from among halogen radicals, preferably F, Cl, Br, particularly preferably F, alkoxy groups, aryloxy groups, carbonyl groups, ester groups, amino groups, amide radicals, $CHF_2$, $CH_2F$, $CF_3$, CN, thio groups and SCN; very particularly preferably methylene, ethylene or 1,4-phenylene;
p is 0 or 1, preferably 0;
q is 0 or 1, preferably 0;
$Y^3$ is hydrogen or an alkyl, aryl, heteroaryl or alkenyl radical, preferably hydrogen or an alkyl or aryl radical, or

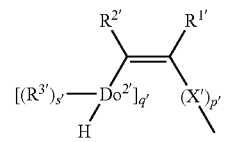

where $Do^{2'}$, q', s', $R^{3'}$, $R^{1'}$, $R^{2'}$, X' and p' are each, independently of one another, as defined for $Do^2$, q, s, $R^3$, $R^1$, $R^2$, X and p;
$R^1$, $R^2$ are each, independently of one another, hydrogen or an alkyl, aryl, heteroaryl or alkenyl radical, preferably hydrogen, an alkyl radical or aryl radical; or
$R^1$ and $R^2$ together form a bridge having a total of from three to five, preferably four, atoms of which one or two atoms may be heteroatoms, preferably N, and the remaining atoms are carbon atoms, so that the group

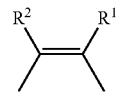

forms a five- to seven-membered, preferably six-membered, ring which may, if appropriate, contain, in addition to the existing double bond, one further double bond or in the case of a six- or seven-membered ring two further double bonds and may optionally be substituted by alkyl, heteroaryl or aryl groups and may, if appropriate, comprise at least one heteroatom, preferably N, with a six-membered aromatic ring which is substituted by alkyl or aryl groups or is unsubstituted being preferred, or the preferred six-membered aromatic ring is fused with further rings which may, if appropriate, comprise at least one heteroatom, preferably N, preferably six-membered aromatic rings;

R³ is hydrogen or an alkyl, aryl, heteroaryl or alkenyl radical, preferably hydrogen or an alkyl, heteroaryl or aryl radical, Y¹, Y² together form a bridge between the nitrogen atoms N which has at least two atoms of which at least one is a carbon atom and the further atoms are preferably nitrogen or carbon atoms, where the bridge can be saturated or unsaturated and the two or more atoms of the bridge may be substituted or unsubstituted and when the bridge has two carbon atoms and is saturated at least one of the two carbon atoms is substituted; where the bridge preferably has two atoms which may be substituted and is unsaturated.

Preferred and very particularly preferred embodiments of the symbols in the novel transition metal complex of the formula IC have been mentioned above in respect of the transition metal complexes used according to the present invention.

As a function of the substitution pattern on the central metal M¹ and when using a central metal having the coordination number 6, for example Ir(III), the octahedral transition metal complexes can be present in the form of their facial or meridional isomers or as a mixture of facial and meridional isomers in any ratios. The conditions for forming facial and meridional isomers have been explained above. The present invention thus likewise provides, apart from fac/mer isomer mixtures, the pure facial or meridional isomers of the transition metal complexes IC of the invention, if these can occur as a result of the substitution pattern on the central metal used. Depending on the properties of the facial or meridional isomers of the transition metal complexes of the formula IB, preference can be given to using either an isomerically pure facial isomer or an isomerically pure meriodional isomer or an isomer mixture of facial and meridional isomers in which one of the isomers is present in excess or the two isomers are present in equal amounts. The individual isomers can be isolated from the corresponding isomer mixture by, for example, chromatography, sublimation or crystallization. Appropriate methods of separating the isomers are known to those skilled in the art.

The group

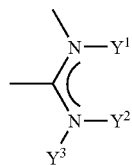

in the transition metal complex IC of the present invention is preferably selected from the group consisting of

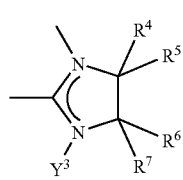
a

-continued

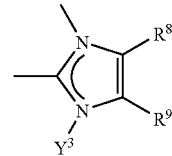
b

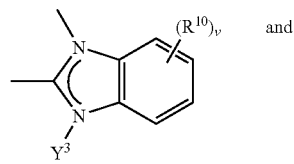
and
c

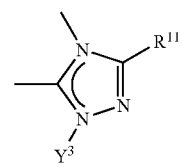
d where the symbols have the following meanings:

$R^4, R^5, R^6$, $R^7, R^8, R^9$ and $R^{11}$ are each, independently of one another, hydrogen, alkyl, aryl, heteroaryl, alkenyl or a substituent which acts as a donor or acceptor and is preferably selected from among halogen radicals, preferably F, Cl, Br, particularly preferably F, alkoxy radicals, aryloxy radicals, carbonyl radicals, ester radicals, amine radicals, amide radicals, $CH_2F$ groups, $CHF_2$ groups, $CF_3$ groups, CN groups, thio groups and SCN groups, preferably hydrogen, alkyl or aryl; where, in the formula a, at least one of the radicals $R^4$, $R^5$, $R^6$ and $R^7$ is not hydrogen;

$R^{10}$ is alkyl, aryl, heteroaryl, alkenyl, preferably alkyl or aryl, or 2 radicals $R^{10}$ together form a fused-on ring which may, if appropriate, comprise one or more heteroatoms, preferably N, preferably form a fused-on aromatic $C_6$ ring, where one or more further aromatic rings may be fused on to this, preferably six-membered, aromatic ring in any conceivable fashion and the fused-on radicals may in turn be substituted; or $R^{10}$ is a radical which acts as a donor or acceptor, preferably selected from among halogen radicals, preferably F, Cl, Br, particularly preferably F; alkoxy, aryloxy, carbonyl, ester, amino groups, amide radicals, $CHF_2$, $CH_2F$, $CF_3$, CN, thio groups and SCN;

v is from 0 to 4, preferably 0, 1 or 2, very particularly preferably 0, where, when v is 0, all 4 possible carbon atoms on the aryl radical in formula c which are optionally substituted by $R^{10}$ bear hydrogen atoms;

$Y^3$ has been defined above.

The group

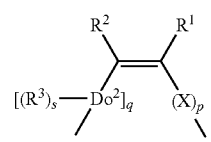

is preferably

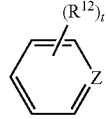

where the symbols have the following meanings:

Z is CH or N and can be located in the o, m or p position relative to the point of linkage of the group to the carbene ligand;

$R^{12}$ is an alkyl, aryl, heteroaryl or alkenyl radical, preferably an alkyl or aryl radical, or 2 radicals $R^{12}$ together form a fused-on ring which may, if appropriate, comprise one or more heteroatoms, preferably N, preferably form a fused-on aromatic $C_6$ ring, where one or more further aromatic rings may, if appropriate, be fused onto this, preferably six-membered, aromatic ring in any conceivable fashion, and the fused-on radicals may in turn be substituted; or $R^{12}$ is a radical which acts as a donor or acceptor, preferably selected from the group consisting of halogen radicals, preferably F, Cl, Br, particularly preferably F; alkoxy, aryloxy, carbonyl, ester, amino groups, amide radicals, $CHF_2$, $CH_2F$, $CF_3$, CN, thio groups and SCN;

t is 0 to 3 and when t>1 the radicals $R^{12}$ can be identical or different; t is preferably 0 or 1 and when t is 1 the radical $R^{12}$ is located in the ortho, meta or para position relative to the point of linkage to the spacer X or, when p is 0, to the point of linkage to the nitrogen atom adjacent to the carbene carbon.

$Y^3$ can be identical to or different from the above-defined group.

The transition metal complex of the present invention particularly preferably has at least two carbene ligands which are selected independently from the group consisting of

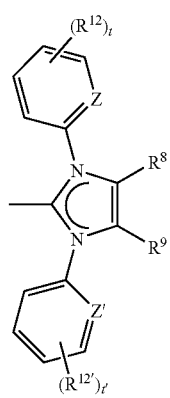

b

-continued

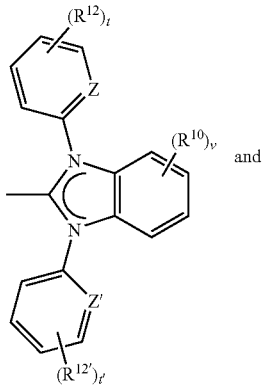

c and

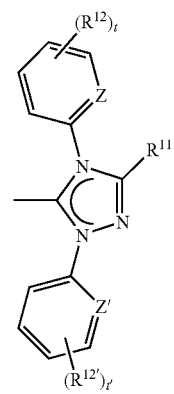

d where the symbols have the following meanings:

Z, Z' are identical or different, preferably identical, and are each CH or N;

$R^{12}$, $R^{12'}$ are identical or different, preferably identical, and are each an alkyl, aryl, heteroaryl or alkenyl radical, preferably an alkyl, heteroaryl or aryl radical, or 2 radicals $R^{12}$ or $R^{12'}$ together form a fused-on ring which may, if appropriate, comprise one or more heteroatoms, preferably N, preferably form a fused-on aromatic $C_6$ ring, where one or more further aromatic rings may, if appropriate, be fused onto this, preferably six-membered, aromatic ring in any conceivable fashion, and the fused-on radicals may in turn be substituted; or $R^{12}$ or $R^{12'}$ is a radical which acts as a donor or acceptor, preferably selected from the group consisting of halogen radicals, preferably F, Cl, Br, particularly preferably F; alkoxy, aryloxy, carbonyl, ester, amino groups, amide radicals, $CHF_2$, $CH_2F$, $CF_3$, CN, thio groups and SCN;

t and t' are identical or different, preferably identical, and are each 0 to 3 and when t>1 the radicals $R^{12}$ or $R^{12'}$ can be identical or different; t or t' is preferably 0 or 1 and when t or t' is 1 the radical $R^{12}$ or $R^{12'}$ is located in the ortho, meta or para position relative to the point of linkage to the nitrogen atom adjacent to the carbene carbon;

$R^8$, $R^9$ and $R^{11}$ are each hydrogen, alkyl, aryl, heteroaryl, alkenyl or a substituent which acts as a donor or acceptor and is preferably selected from among halogen radicals, preferably F, Cl, Br, particularly preferably F, alkoxy radicals, aryloxy radicals, carbonyl radicals, ester radicals, amine radicals, amide radicals, $CH_2F$ groups, $CHF_2$ groups, $CF_3$ groups, CN groups, thio groups and SCN groups, preferably hydrogen, alkyl or aryl;

$R^{10}$ is alkyl, aryl, heteroaryl, alkenyl, preferably alkyl, heteroaryl or aryl, or 2 radicals $R^{10}$ together form a fused-on ring which may, if appropriate, comprise one or more heteroatoms, preferably N, preferably form a fused-on aromatic $C_6$ ring, where one or more further aromatic rings may, if appropriate, be fused on to this, preferably six-membered, aromatic ring in any conceivable fashion and the fused-on radicals may in turn be substituted; or $R^{10}$ is a radical which acts as a donor or acceptor, preferably selected from among halogen radicals, preferably F, Cl, Br, particularly preferably F; alkoxy, aryloxy, carbonyl, ester, amino groups, amide radicals, $CHF_2$, $CH_2F$, $CF_3$, CN, thio groups and SCN;

v is from 0 to 4, preferably 0, 1 or 2, very particularly preferably 0, where, when v is 0, all 4 possible carbon atoms on the aryl radical in formula c which are optionally substituted by $R^{10}$ bear hydrogen atoms.

The novel transition metal complexes of the formula IC particularly preferably contain a metal atom $M^1$ selected from the group consisting of Rh(III), Ir(III), Ru(III), Ru(IV) and Pt(II), preferably Pt(II) or Ir(III). Particular preference is given to using Ir, preferably Ir(III), as metal atom $M^1$.

In a very particularly preferred embodiment, $M^1$ in the transition metal complexes of the present invention is Ir(III), n is 3 and m and o are each 0 with particular preference being given to the three carbene ligands being identical.

The novel transition metal complexes of the formula IC can be prepared by methods analogous to those known to a person skilled in the art. Suitable preparative methods are described, for example, in the review articles W. A. Hermann et al., Advances in Organometallic Chemistry, Vol. 48, 1 to 69, W. A. Hermann et al., Angew. Chem. 1997, 109, 2256 to 2282 and G. Bertrand et al. Chem. Rev. 2000, 100, 39 to 91 and the literature cited therein.

In one embodiment, the transition metal complexes of the present invention are prepared by deprotonation of the ligand precursors corresponding to the appropriate carbene ligands and subsequent reaction with suitable metal complexes comprising the desired metal. The transition metal complexes of the present invention can also be prepared by direct use of Wanzlick olefins.

Suitable ligand precursors are known to those skilled in the art. They are preferably cationic precursors.

In a preferred embodiment, the cationic precursors are deprotonated, which can result in different intermediates depending on the precursor. Thus, for example, alkoxide derivatives, dimeric Wanzlick olefins or the free N-heterocycle carbenes can be formed depending on the way in which the reaction is carried out. Alkoxide derivatives and Wanzlick olefins are preferably treated thermally in the presence of a suitable metal precursor, resulting in elimination of the alcohol or dissociation of the dimer and formation of the metal-carbene compound in the presence of suitable metal complexes. If the free carbene is formed as intermediate, the reaction is preferably carried out with cooling and subsequent warming to room temperature and, if necessary, further heating. The reactions are preferably carried out in suitable solvents. In the case of two-stage variants, the two substeps can be carried out using the same solvent or different solvents. Suitable solvents are, for example, aromatic and aliphatic solvents or ethers, for example toluene, tetrahydrofuran. If free carbenes are not employed, it is also possible to use alcohols or chlorinated hydrocarbons such as methylene chloride. To prepare free carbenes, it is also possible to use liquid ammonia, if appropriate in admixture with tetrahydrofuran, as solvent.

The present invention therefore further provides a process for preparing the novel transition metal complexes of the formula IC by deprotonation of the ligand precursors corresponding to the appropriate carbene ligands and subsequent reaction with suitable metal complexes comprising the desired metal.

The deprotonation of the ligand precursors can be carried out by means of basic metalates, basic anions such as metal acetates, acetylacetonates or alkoxylates or external bases such as $KO^tBu$, $NaO^tBu$, $LiO^tBu$, NaH, silylamides, amides and phosphazene bases.

The novel transition metal complexes of the formula IC bearing N-heterocyclic carbene ligands are preferably reacted by deprotonation of the appropriate cationic precursors selected from the group consisting of azolium salts, in particular imidazolium salts, benzimidazolium salts; triazolium salts and azolidinium salts, in particular imidazolidinium salts, by means of an external base, preferably $KO^tBu$ or silylamines, particularly preferably silylamides, e.g. potassium bis(trimethylsilyl)amide. The intermediate obtained is subsequently reacted with a complex of the desired metal.

Suitable complexes of the desired metal are known to those skilled in the art. The desired metal in the metal complex used and the corresponding metal of the transition metal complex IC prepared therefrom do not have to be in the same oxidation state.

In the preparation of iridium(III) complexes of the formula IC, which are particularly preferred according to the present invention, it is possible to use, for example, the following iridium (III) complexes: $[(\mu\text{-Cl})Ir(\eta^4\text{-1,5-cod})]_2$, $[(\mu\text{-Cl}) Ir(\eta^2\text{-1,5-coe})_2]_2$, $Ir(acac)_3$, $IrCl_3 \times n\ H_2O$, $(tht)_3IrCl_3$, where cod is cyclooctadiene, coe is cyclooctene, acac is acetylacetonate and tht is tetrahydrothiophene.

The reaction is preferably carried out in a solvent. Suitable solvents are preferably selected from the group consisting of aromatic, aliphatic solvents, ethers, alcohols and halogenated hydrocarbons. Alcohols and halogenated hydrocarbons are generally used only when no free carbene is formed in the reaction. Furthermore, liquid ammonia can be used as solvent for generating free carbenes.

Alkoxide derivatives or Wanzlick olefins are usually added to the appropriate metal precursors at room temperature and subsequently treated thermally, which results in the corresponding alcohol being eliminated in the case of the alkoxide derivatives or the dimeric Wanzlick olefins being dissociated and the metal-carbene compound being formed. Temperatures of from 20 to 120° C., preferably from 25 to 110° C., are usually suitable for this reaction. If free carbenes are used as intermediates (e.g. imidazolin-2-ylidene), these are preferably firstly added to the metal precursor with cooling, after which the mixture is warmed to room temperature (20-25° C.) and, if appropriate, subsequently heated further. Temperatures of from −78 to +120° C. are thus suitable for this reaction.

The ratio of metal complex used to ligand precursor used is dependent on the desired complex bearing at least two carbene ligands. If the metal atom is Ir(III), which is particularly preferred, and the desired transition metal complex comprises three carbene ligands, which is likewise particularly preferred, then the molar amount of ligand precursors has to be about three times the molar amount of metal in the metal complex. A small excess of the ligand precursor can be used. The molar ratio of metal in the metal complex to the molar amount of ligand precursors is preferably from 1:3 to 1:5, particularly preferably from 1:3 to 1:4.

The molar amount of the base used is dependent on the molar amount of the ligand precursor used; the base and the ligand precursor are used in a molar ratio of from 2:1 to 1:1, preferably from 1.5:1 to 1.2:1.

The preparation of two iridium complexes with N-heterocyclic carbene ligands according to the present invention is described below by way of example:

Imidazolinylidene Complex:

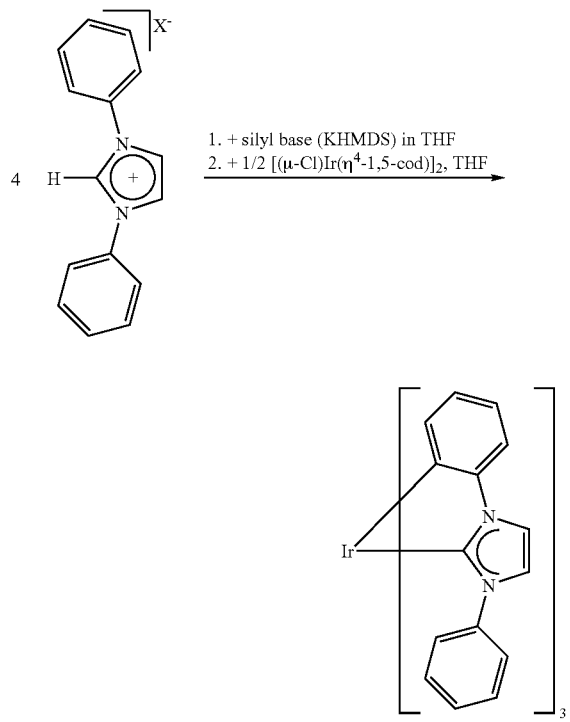

X⁻ is an anionic group, preferably a halide, pseudohalide or another monoanionic group, for example Cl⁻, Br⁻, BF₄⁻, PF₆⁻, CN⁻, SCN⁻, particularly preferably BF₄⁻, PF₆⁻.

Benzimidazolinylidene Complex:

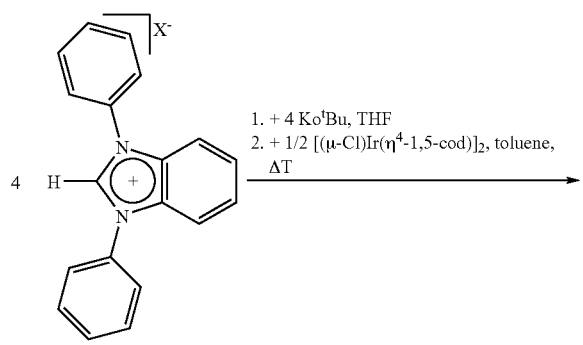

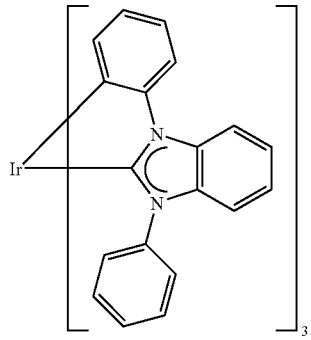

X⁻ has been defined above.

The transition metal-carbene complexes used according to the present invention are very useful as emitter substances since they display emission (electroluminescence) in the visible region of the electromagnetic spectrum. The use of the transition metal-carbene complexes used according to the present invention as emitter substances makes it possible to provide compounds which display electroluminescence in the red, green or blue region of the electromagnetic spectrum. It is thus possible to obtain industrially usable full-color displays using the transition metal-carbene complexes used according to the present invention as emitter substances.

The ready availability of various substituted carbene ligands and various transition metals makes it possible to prepare emitter substances which emit light in various regions of the electromagnetic spectrum. The quantum yield is high and the stability of the transition metal-carbene complexes, in particular complexes bearing N-heterocyclic carbene ligands, in the device is high.

Furthermore, the abovementioned uncharged transition metal complexes are suitable as electron blockers, exciton blockers or hole blockers in OLEDs, depending on the ligands used and the central metal used.

Organic light-emitting diodes are basically made up of a plurality of layers. (Cf. FIG. 1)
1. Anode
2. Hole transport layer
3. Light-emitting layer
4. Electron transport layer
5. Cathode However, it is also possible for the OLED not to have all of the layers mentioned; for example, an OLED having the layers (1) (anode), (3) (light-emitting layer) and (5) (cathode) in which the functions of the layers (2) (hole transport layer) and (4) (electron transport layer) are taken over by the adjoining layers is likewise suitable. OLEDs having the layers (1), (2), (3) and (5) or the layers (1), (3), (4) and (5) are likewise suitable.

The transition metal-carbene complexes according to the present patent application can be used in various layers of an OLED. The present invention therefore further provides an OLED comprising at least one transition metal-carbene complex according to the present patent application. The transition metal-carbene complexes are preferably used as emitter molecules in the light-emitting layer. The present invention therefore also provides a light-emitting layer comprising at least one transition metal-carbene complex as emitter molecule. Preferred transition metal-carbene complexes, in particular transition metal-carbene complexes bearing N-heterocyclic carbene ligands, have been mentioned above.

The transition metal-carbene complexes of the present invention or those used according to the present invention can be present in bulk, i.e. without further additives, in the light-emitting layer or another layer of the OLED, preferably in the light-emitting layer. However, it is likewise possible for further compounds in addition to the transition metal-carbene complexes used according to the present invention to be present in the layers comprising at least one transition metal-carbene complex according to the present patent application, preferably in the light-emitting layer. For example, a fluorescent dye can be present in the light-emitting layer in order to alter the emission color of the transition metal-carbene complex used as emitted molecule. Furthermore, a diluent material can be used. This diluent material can be a polymer, for example poly(N-vinylcarbazole) or polysilane. However, the diluent material can likewise be a small molecule, for example 4,4'-N,N'-dicarbazolylbiphenyl (CDP=CBP) or tertiary aromatic amines. If a diluent material is used, the proportion of transition metal-carbene complexes used according to the present invention in the light-emitting layer is generally less than 30% by weight, preferably less than 20% by weight, particularly preferably from 3 to 10% by weight.

The individual layers as described above of the OLEDs can in turn be made up of 2 or more layers. For example, the hole transport layer can be made up of a layer into which holes are injected from the electrode and a layer which transports the holes from the hole injection layer into the light-emitting layer. The electron transport layer can likewise consist of a plurality of layers, for example a layer into which electrons are injected by means of the electrode and a layer which receives electrons from the electron injection layer and transports them to the light-emitting layer. These layers are in each case selected according to factors such as energy level, heat resistance and charge carrier mobility and also the energy difference between the respective layer and the organic layers or the metal electrodes. A person skilled in the art will be able to select the structure of the OLEDs so that it is matched optimally to the transition metal-carbene complexes used according to the present invention as emitter substances.

To obtain particularly efficient OLEDs, the HOMO (highest occupied molecular orbital) of the hole transport layer should be matched to the work function of the anode and the LUMO (lowest unoccupied molecular orbital) of the electron transport layer should be matched to the work function of the cathode.

The present invention further provides an OLED comprising at least one light-emitting layer according to the present invention. The further layers in the OLED can be made up of any material which is customarily used in such layers and is known to those skilled in the art.

The anode (1) is an electrode which provides positive charge carriers. It can, for example, be made up of materials which comprise a metal, a mixture of various metals, a metal alloy, a metal oxide or a mixture of various metal oxides. As an alternative, the anode can be a conductive polymer. Suitable metals comprise the metals of groups 11, 4, 5 and 6 of the Periodic Table of the Elements and the transition metals of groups 8 to 10. If the anode is to allow light to pass through it, use is generally made of mixed oxides of metals of groups 12, 13 and 14 of the Periodic Table of the Elements, for example indium-tin oxide (ITO). It is likewise possible for the anode (1) to comprise an organic material, for example polyaniline, as described, for example, in Nature, Vol. 357, pages 477 to 479 (Jun. 11, 1992). At least one of the anode and cathode should be at least partially transparent to allow the light produced to be emitted from the OLED.

Suitable hole transport materials for the layer (2) of the OLED of the present invention are disclosed, for example, in Kirk-Othmer Encyclopedia of Chemical Technology, 4$^{th}$ Edition, Vol. 18, pages 837 to 860, 1996. Both hole-transporting molecules and polymers can be used as hole transport material. Hole-transporting molecules customarily used are selected from the group consisting of 4,4'-bis[N-(1-naphthyl)-N-phenylamino]biphenyl (α-NPD), N,N'-diphenyl-N,N'-bis(3-methylphenyl)[1,1'-bi-phenyl-4,4'-diamine] (TPD), 1,1-bis[(di-4-tolylamino)phenyl]cyclohexane (TAPC), N,N'-bis(4-methylphenyl)-N,N'-bis(4-ethylphenyl) [1,1'-(3,3'-dimethyl)biphenyl-4,4'-diamine] (ETPD), N,N,N',N'-tetrakis-(3-methylphenyl)phenylene-2,5-diamine (PDA), α-phenyl-4-N,N-diphenylaminostyrene (TPS), p-(diethylamino)benzaldehyde diphenyl-hydrazone (DEH), triphenylamine (TPA), bis[4-(N,N-diethylamino)-2-methylphenyl)-(4-methylphenyl)methane (MPMP), 1-phenyl-3-[p-(diethylamino)styryl]-5-[p-(diethyl-amino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB) 4,4',4"-tris(N,N-diphenylamino)triphenylamine (TDTA) and porphyrin compounds and phthalocyanines such as copper phthalocyanines. Hole-transporting polymers customarily used are selected from the group consisting of polyvinylcarbazoles, (phenylmethyl)polysilanes, PEDOT (poly(3,4-ethylenedioxythiophene), preferably PEDOT doped with PSS (polystyrenesulfonate), and polyanilines. It is likewise possible to obtain hole-transporting polymers by doping polymers such as polystyrene and polycarbonate with hole-transporting molecules. Suitable hole-transporting molecules are the molecules which have been mentioned above.

Suitable electron transport materials for the layer (4) of the OLEDs of the present invention comprise metal chelated with oxinoid compounds, e.g. tris(8-hydroxy-quinolato)aluminum ($Alq_3$), compounds based on phenanthroline, e.g. 2,9-dimethyl-4,7-diphenyl-1,10-phenanthroline (DDPA=BCP) or 4,7-diphenyl-1,10-phenanthroline (DPA), and azole compounds such as 2-(4-biphenylyl)-5-(4-t-butylphenyl)-1,3,4-oxa-diazole (PBD) and 3-(4-biphenylyl)-4-phenyl-5-(4-t-butylphenyl)-1,2,4-triazole (TAZ). The layer (4) can either aid electron transport or serve as buffer layer or barrier layer to avoid quenching of the excitons at the interfaces of the layers of the OLED. The layer (4) preferably improves the mobility of the electrons and reduces quenching of the excitons.

Among the materials mentioned above as hole transport materials and electron transport materials, some can perform a plurality of functions. For example, some of the electron-conducting materials simultaneously act as hole-blocking materials if they have a low HOMO.

The charge transport layers can also be electronically doped to improve the transport properties of the materials used so as firstly to make the layer thicknesses more generous (avoidance of pinholes/short circuits) and secondly to minimize the operating voltage of the device. For example, the hole transport materials can be doped with electron acceptors; e.g. phthalocyanines or arylamines such as TPD or TDTA can be doped with tetrafluorotetracyanoquinodimethane (F4-TCNQ). The electron transport materials can, for example, be doped with alkali metals; for example, $Alq_3$ can be doped with lithium. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003, and Pfeiffer et al., Organic Electronics 2003, 4, 89-103.

The cathode (5) is an electrode which serves to introduce electrons or negative charge carriers. The cathode can be any metal or nonmetal which has a lower work function than the cathode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. Furthermore, metals such as aluminum, indium, calcium, barium, samarium and magnesium and also combinations thereof can be used. In addition, lithium-comprising organometallic compounds or LiF can be applied between the organic layer and the cathode to reduce the operating voltage.

The OLED of the present invention can further comprise additional layers known to those skilled in the art. For example, a layer which aids transport of positive charges and/or fits the band gap of the layers to one another can be applied between the layer (2) and the light-emitting layer (3). This further layer can alternatively serve as a protective layer. In an analogous manner, additional layers can be present between the light-emitting layer (3) and the layer (4) to aid transport of negative charges and/or fit the band gap of the layers to one another. This layer can alternatively serve as protective layer.

In a preferred embodiment, the OLED of the present invention further comprises, in addition to the layers (1) to (5), at least one of the following additional layers:
- a hole injection layer between the anode (1) and the hole transport layer (2);
- a blocking layer for electrons and/or excitons between the hole transport layer (2) and the light-emitting layer (3);
- a blocking layer for holes and/or excitons between the light-emitting layer (3) and the electron transport layer (4);
- an electron injection layer between the electron transport layer (4) and the cathode (5).

However, it is also possible for the OLED not to have all of the abovementioned layers (1) to (5); for example, an OLED having the layers (1) (anode), (3) (light-emitting layer) and (5) (cathode) in which the functions of the layers (2) (hole transport layer) and (4) (electron transport layer) are taken over by the adjoining layers is likewise suitable. OLEDs which have the layers (1), (2), (3) and (5) or the layers (1), (3), (4) and (5) are likewise suitable.

A person skilled in the art will be familiar with the selection of suitable materials (for example on the basis of electrochemical tests). Suitable materials for the individual layers are known to those skilled in the art and disclosed, for example, in WO 00/70655.

Furthermore, each of the abovementioned layers of the OLED of the present invention can be made up of two or more layers. It is also possible for some or all of the layers (1), (2), (3), (4) and (5) to have been surface-treated in order to increase the efficiency of charge carrier transport. The materials for each of the layers mentioned are preferably chosen so as to obtain an OLED having a high efficiency.

The OLED of the present invention can be produced by methods known to those skilled in the art. In general, the OLED is produced by successive vapor deposition of the individual layers on a suitable substrate. Suitable substrates include, for example, glass or polymer films. Vapor deposition can be carried out using customary techniques such as thermal vaporization, chemical vapor deposition and others. In an alternative process, the organic layers can be applied from solutions or dispersions in suitable solvents using coating techniques known to those skilled in the art. Compositions which comprise, in addition to the at least one transition metal-carbene complex according to the invention, a polymeric material in one of the layers of the OLED, preferably in the light-emitting layer, are generally applied as a layer by means of solution processing methods.

In general, the various layers have the following thicknesses: anode (2) 500-5 000 Å, preferably 1 000-2 000 Å; hole transport layer (3) 50-1 000 Å, preferably 200-800 Å, light-emitting layer (4) 10-1 000 Å, preferably 100-800 Å, electron transport layer (5) 50-1 000 Å, preferably 200-800 Å, cathode (7) 200-10 000 Å, preferably 300-5 000 Å. The position of the recombination zone of holes and electrons in the OLED of the present invention and thus the emission spectrum of the OLED can be influenced by the relative thickness of the layers. This means that the thickness of the electron transport layer should preferably be selected so that the electron/hole recombination zone is located in the light-emitting layer. The ratio of the thicknesses of the individual layers in the OLED is dependent on the materials used. The thicknesses of any additional layers used are known to those skilled in the art.

Use of the transition metal-carbene complexes used according to the present invention in at least one layer of the OLED of the invention, preferably as emitter molecules in the light-emitting layer of the OLEDs of the present invention enables OLEDs having a high efficiency to be obtained. The efficiency of the OLEDs of the present invention can also be improved by optimizing the other layers. For example, high-efficiency cathodes such as Ca, Ba or LiF can be used. Shaped substrates and new hole transport materials which reduce the operating voltage or increase the quantum efficiency can likewise be used in the OLEDs of the present invention. Furthermore, additional substances can be present in the OLEDs in order to adjust the energy level of the various layers and to assist electroluminescence.

The OLEDs of the present invention can be employed in all devices in which electroluminescence is useful. Suitable devices are preferably selected from among stationary and mobile VDUs. Stationary VDUs include, for example, VDUs of computers, televisions, VDUs in printers, kitchen appliances and advertising signs, lighting units and information signs. Mobile VDUs include, for example, VDUs in mobile telephones, laptops, digital cameras, vehicles and destination displays on buses and trains.

Furthermore, the transition metal-carbene complexes used according to the invention can be employed in OLEDs having an inverse structure. In these inverse OLEDs, the transition metal-carbene complexes are once again preferably used in the light-emitting layer. The structure of inverse OLEDs and the materials customarily used therein are known to those skilled in the art.

The above-described transition metal complexes of the present invention or those used according to the present invention can not only be employed in OLEDs but also as colorants which emit in the visible region of the electromagnetic spectrum on irradiation with light (photoluminescence). Such colorants are preferably used as colorants in polymeric materials.

The present invention therefore also provides for the use of the above-described transition metal complexes of the present invention or those used according to the present invention for coloring polymeric materials.

Suitable polymeric materials include polyvinyl chloride, cellulose acetate, poly-carbonates, polyamides, polyurethanes, polyimides, polybenzimidazoles, melamine resins, silicones, polyesters, polyethers, polystyrene, polymethyl methacrylate, polyethylene, polypropylene, polyvinyl acetate, polyacrylonitrile, polybutadiene, polychlorobutadiene, polyisoprene and copolymers of the monomers listed.

Furthermore, the above-described transition metal complexes of the present invention or those used according to the present invention can be employed in the following applications:

- Use of the transition metal complexes as or in vat dye(s), for example for coloring natural materials such as paper, wood, straw, leather, pelts or natural fiber materials such as cotton, wool, silk, jute, sisal, hemp, flax or animal hairs (for example horsehair) and their conversion products such as viscose fibers, nitrate silk or copper rayon (Reyon).
- Use of the transition metal complexes as dyes, for example for coloring paints, varnishes and other surface coating compositions, paper colors, printing inks, inks and other colors for drawing and writing purposes.
- Use of the transition metal complexes as pigments, for example for coloring paints, varnishes and other surface coating compositions, paper colors, printing inks, inks and other colors for drawing and writing purposes.
- Use of the transition metal complexes as pigments in electrophotography: for example for dry copying systems (Xerox process) and laser printers.
- Use of the transition metal complexes for safety marking purposes in which good chemical and photochemical stability and if appropriate also the luminescence of the substances is of importance. This is preferably for checks, check cards, coupons having a monetary value, documents, identification papers and the like in which a particular, unmistakable color impression is to be achieved.
- Use of the transition metal complexes as additives to other colors in which a particular color shade is to be achieved, preferably particularly brilliant colors.
- Use of the transition metal complexes for marking articles for instrumental recognition of these articles by means of the luminescence, preferably instrumental recognition of articles for sorting purposes, for example in the recycling of plastics.
- Use of the transition metal complexes as luminescent dyes for machine-readable markings, preferably alphanumeric markings or bar codes.
- Use of the transition metal complexes for changing the frequency of light, for example to convert short-wavelength light into longer-wavelength, visible light.
- Use of the transition metal complexes in display elements for a wide variety of display, information and marking purposes, for example in passive display elements, information signs and traffic signs, e.g. traffic lights.
- Use of the transition metal complexes in ink jet printers, preferably in homogeneous solution as luminescent ink.
- Use of the transition metal complexes as starting material for superconducting organic materials.
- Use of the transition metal complexes for solid-state luminescent markings.
- Use of the transition metal complexes for decorative purposes.
- Use of the transition metal complexes for tracer purposes, for example in biochemistry, medicine, engineering and natural sciences. Here, the dyes can be bound covalently to substrates or be bound via secondary valences such as hydrogen bonds or hydrophobic interactions (adsorption).
- Use of the transition metal complexes as luminescent dyes in high-sensitivity detection methods (cf. C. Aubert, J. Fünfschilling, I. Zschocke-Gränacher and H. Langhals, Z. Analyt. Chem. 320 (1985) 361).
- Use of the transition metal complexes as luminescent dyes in scintillation devices.
- Use of the transition metal complexes as dyes or luminescent dyes in optical light-collection systems.
- Use of the transition metal complexes as dyes or luminescent dyes in luminescent solar collectors (cf. Langhals, Nachr. Chem. Tech. Lab. 28 (1980) 716).
- Use of the transition metal complexes as dyes or luminescent dyes in luminescence-activated displays (cf. W. Greubel and G. Baur, Elektronik 26 (1977) 6).
- Use of the transition metal complexes as dyes or luminescent dyes in cold light sources for light-induced polymerization for the preparation of polymers.
- Use of the transition metal complexes as dyes or luminescent dyes for materials testing, for example in the production of semiconductor circuits.
- Use of the transition metal complexes as dyes or luminescent dyes for the examination of microstructures of integrated semiconductor components.
- Use of the transition metal complexes as dyes or luminescent dyes in photoconductors.
- Use of the transition metal complexes as dyes or luminescent dyes in photographic processes.
- Use of the transition metal complexes as dyes or luminescent dyes in display, illumination or image conversion systems in which excitation occurs by means of electrons, ions or UV radiation, for example in luminescent displays, Braun tubes or in fluorescent tubes.
- Use of the transition metal complexes as dyes or luminescent dyes as part of an integrated semiconductor circuit, either as such or in combination with other semiconductors, for example in the form of epitaxy.
- Use of the transition metal complexes as dyes or luminescent dyes in chemiluminescence systems, for example in chemiluminescent illumination rods, in immunoassays based on luminescence or other detection methods based on luminescence.
- Use of the transition metal complexes as dyes or luminescent dyes as signal colors, for example for optical emphasis of writing and drawings or other graphic products, for individualizing signs and other articles in which a particular optical color impression is to be achieved.
- Use of the transition metal complexes as dyes or luminescent dyes in dye lasers, for example as luminescent dyes for generating laser beams.
- Use of the transition metal complexes as active substances for nonlinear optics, for example for frequency doubling and frequency tripling of laser light.
- Use of the transition metal complexes as rheology improvers.
- Use of the transition metal complexes as dyes in photovoltaic devices for converting electromagnetic radiation into electric energy.

The following examples illustrate the invention.

EXAMPLES

1. Preparation of the Ligands:

The necessary ligand precursors were prepared by methods based on literature methods:

a) Compound (1)

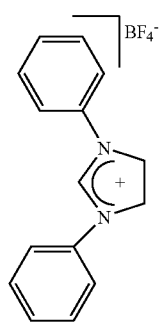

(1)

The synthesis is carried out starting from N,N-diphenylethane-1,2-diamine using a method based on that described in Organic Letters, 1999, 1, 953-956; Angewandte Chemie, 2000, 112, 1672-1674. The bisamine is reacted with triethyl formate in the presence of ammonium tetrafluoroborate.

The compound was obtained after recrystallization from ethanol.

$^1$H-NMR (400 MHz, DMSO):

δ=4.60 (s, 4H, CH$_2$), 7.40 (tt, 2H), 7.57 (dd, 4H), 7.65 (dd, 4H), 9.95 (s, 1H, C$^+$H)

$^{13}$C-NMR (100 MHz, DMSO):

δ=48.2, 118.4, 127.0, 129.6, 136.0, 151.7 b) Compound (2)

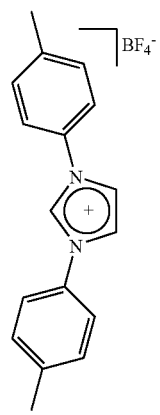

(2)

The synthesis starts, using a method based on that described in Chem. Ber. 1971, 104, 92-109 (in particular page 106), with the preparation of the bisimine of glyoxal and aniline or para-toluidine.

The Schiff bases obtained are converted into the corresponding imidazolium chloride salt by treatment with a hydrochloric acid suspension of paraformaldehyde in dioxane using the method described in Journal of Organometallic Chemistry 2002, 606, 49-54.

Using aniline:

δ=7.64 (t, 2H), 7.72 (t, 4H), 7.93 (d, 4H), 8.60 (d, 2H), 10.75 (s, 1H)

MS (ESI, ACN/H$_2$O 8/2):

m/e=221.0

Using Para-Toluidine:

$^1$H-NMR (500 MHz, DMSO):

δ=2.42 (s, 6H), 7.49 (d, 4H), 7.88 (d, 4H), 8.61 (d, 2H,), 10.52 (t, 1H)

The anion can be replaced by treatment with AgBF$_4$ or NaBF$_4$.

c) Compound (3)

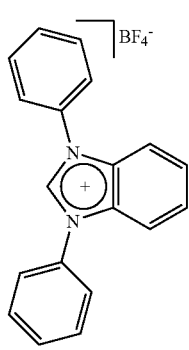

(3)

The synthesis starts out from 1,2-phenylenediamine. After introduction of acetyl groups on the amino functions, the phenyl groups were introduced into the resulting amide with the aid of a copper-catalyzed procedure as described in Synthetic Communications, 2000, 30, 3651-3668. Without purification, the material was treated in boiling ethanolic KOH solution. The product was obtained by chromatography.

$^1$H-NMR (CD$_2$Cl$_2$, 500 MHz):

δ=5.70 (s, broad, 2H), 6.87 (t, 2H), 6.93 (d, 4H), 6.97 (dd, 2H), 7.22 (t, 4H), 7.28 (dd, 2H)

The imidazolium salt required was prepared by treatment of N,N'-diphenylbenzene-1,2-diamine with triethyl orthoformate in the presence of ammonium tetrafluoroborate.

The material was obtained by crystallization.

$^1$H-NMR (DMSO, 400 MHz):

δ=7.74-7.84 (m, 8H), 7.91-7.98 (m, 6H), 10.57 (s, 1H)

d) Compound (4)

da) Preparation of Compound 4a

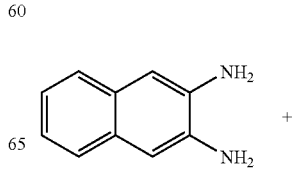

db) Preparation of Compound (4)

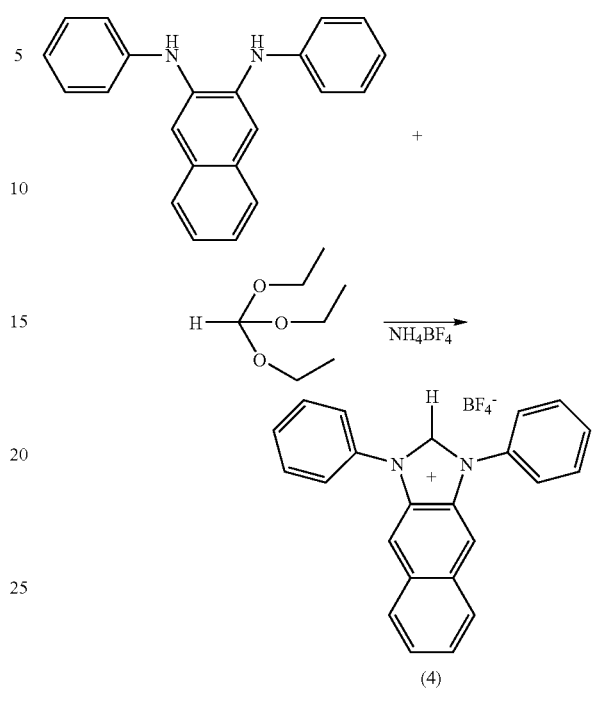

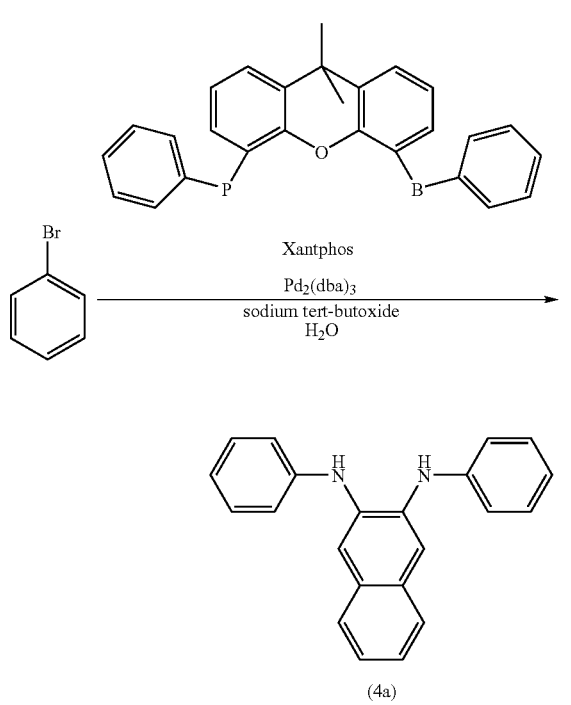

In a countercurrent of argon, 3.16 g (20 mmol) of 2,3-diaminonaphthalene (Acros) and 6.28 g (40 mmol) of distilled bromobenzene (Aldrich) together with 80 ml of toluene (water-free) were placed in a flask which had been flushed with argon. The brown suspension was degassed by application of a vacuum to the flask. Argon was then admitted again and a spatula tip of $Pd_2(dba)_3$, a spatula tip of 9,9-dimethyl-4,5-bis-(diphenylphosphino)xanthene (xantphos), 2.70 g (28 mmol) of sodium tert-butoxide and 0.36 g (20 mmol) of degassed water were added in a countercurrent of argon. The brown suspension was heated to reflux and stirred under reflux for 15 hours. It was then allowed to come to room temperature.

For the work-up, the mixture was diluted with methylene chloride and extracted twice with water, then dried over sodium sulfate, filtered and the filtrate was evaporated under reduced pressure. The residue was purified by column chromatography (silica gel, methylene chloride comprising 5 ml of triethylamine per I of methylene chloride). The fractions comprising the product were combined and freed of the solvent under reduced pressure. This gave 2.7 g (43.5%) of compound (4a).

$^1$H-NMR (CDCl$_3$, 400 MHz):

δ=5.85 (s, broad, NH), 6.97 (tt, 2H, J=7.3 Hz, J=1.2 Hz), 7.07 (dd, 4H, J=8.7 Hz, J=1.1 Hz), 7.28-7.32 (m, 6H), 7.60 (dd, 2H, J=6.1 Hz, J=3.1 Hz), 7.64 (s, 2H)

MS (EI):

m/e=310.0, 311.0, 312.0 (M$^+$)

A two-neck flask was flushed with nitrogen for 20 minutes. 7.68 g (24.74 mmol) of the 2,3-di-N-phenylaminonaphthalene were then dissolved in 51.34 g (346.4 mmol) of triethyl formate at 100° C. and 2.59 g (24.74 mmol) of ammonium tetrafluoroborate were added, also under a countercurrent of nitrogen. The solution was then heated to reflux and stirred under reflux for 12 hours. The reaction mixture was then brought to room temperature.

For the work-up, the reaction mixture was filtered through a G4 frit and the solid was washed with ortho ester. It was then dried at 50° C. in a vacuum drying oven. The material obtained in this way (6.05 g) was dissolved in methylene chloride and filtered by means of a suction filter. The mother liquor was evaporated under reduced pressure and the solid was once again dried at 50° C. in a vacuum drying oven. This gave 5.37 g (53%) of the compound (4).

$^1$H-NMR (0114600902, 400 MHz, CD$_2$Cl$_2$):

δ=7.69 (dd, 2H, J=2.9 Hz, J=6.7 Hz), 7.76-7.82 (m, 6H), 7.91-7.95 (m, 4H), 8.10 (dd, 2H, J=3.3 Hz, J=6.6 Hz), 8.29 (s, somewhat broader, 2H), 9.75 (s, 1H)

Elemental Analysis:

| Exp. | 18.3% F | 67.2% C | 6.8% N | 4.10% H |
| Theor. | 18.6% F | 67.6% C | 6.8% N | 4.16% H |

2. Preparation of the Metal Complexes:

Ir(imidazolidine)$_3$ was prepared by a method based on that of P. B. Hitchcock, M. F. Lappert, P. Terreros, *J. Organomet. Chem.* 1982, 239, C26-C30. Unlike the literature method cited, the imidazolidinium salt rather than the Wanzlick olefin was used as starting material.

Preparation of the metal-carbene complexes (all syntheses described were carried out in pure solvents under an inert gas atmosphere by means of the Schlenk technique):

a) Preparation of an Ir Complex (5)

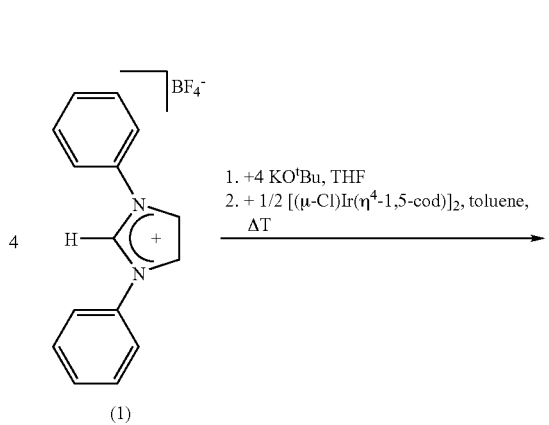

b) Preparation of an Ir Complex (6)

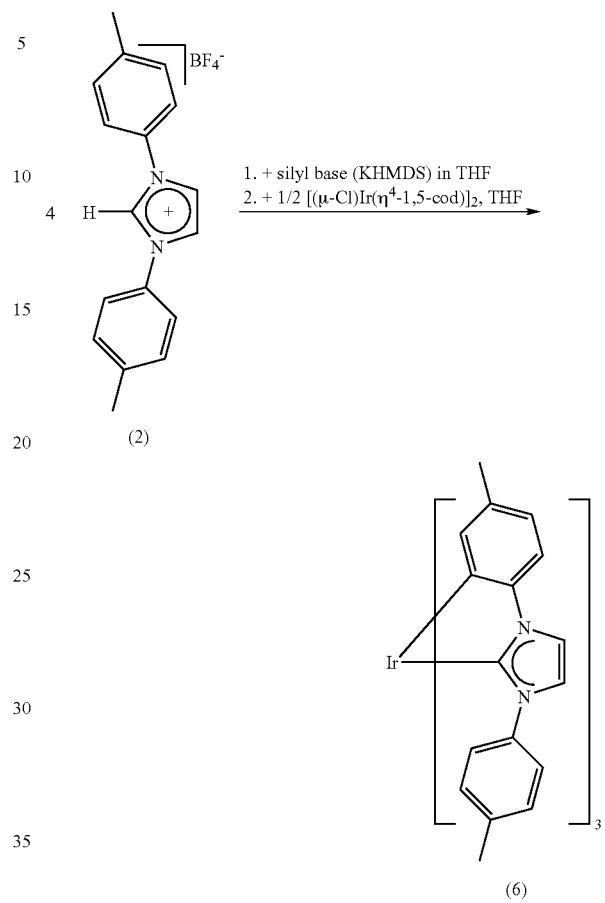

In a 100 ml three-necked flask, 3.0 g (9.6 mmol) of the imidazolium salt (compound (1)) were suspended in 40 ml of tetrahydrofuran. The light-brown suspension was admixed at room temperature with a solution of 1.11 g (9.7 mmol) of KO$^t$Bu in 10 ml of THF. The mixture was stirred at room temperature for one hour and subsequently evaporated to dryness. After the solid had been taken up again in 30 ml of toluene, the resulting suspension was added to a solution of 820 mg (1.2 mmol) of [(μ-Cl)(η$^4$-1,5-cod)Ir]$_2$ in 20 ml of toluene. The reaction mixture was refluxed for 2 hours, stirred overnight at room temperature and subsequently refluxed for another 3.5 hours. It was then allowed to cool to room temperature. The precipitate was filtered off, washed with toluene, extracted with methylene chloride and the methylene chloride was removed under reduced pressure. The residue was subjected to purification by column chromatography. This gave a light-yellow powder (240 mg, 15%).

$^{13}$C-NMR (CD$_2$Cl$_2$, 125 MHz): 200.0 (NCN), 149.3, 146.5, 142.5 (each C$_q$ or IrC$_{phenyl}$), 134.5, 127.2, 126.5, 125.5, 120.6, 119.7, 106.8 (each CH$_{phenyl}$), 53.8, 44.1 (NCH$_2$CH$_2$N).

Mass (EI): m/e=856.

Optical spectroscopy: λ=533 nm (main maximum of the powder).

In a 100 ml three-necked flask, 0.92 g (2.7 mmol) of the imidazolium salt (compound (2)) was dissolved in 20 ml of tetrahydrofuran. At −8° C., 547 ml of base (0.5 M in toluene, 2.8 mmol) were added over a period of 10 minutes and the mixture was stirred at room temperature for 1 hour.

310 mg (0.460 mmol) of [(μ-Cl)(η$^4$-1,5-cod)Ir]$_2$ were dissolved in 20 ml of THF, cooled to −78° C. and the salt mixture was added dropwise to this solution. The mixture was stirred for 2 hours at 60° C., overnight at room temperature, for 8 hours under reflux and subsequently overnight at room temperature. After filtration, the solution was evaporated to dryness and the brown residue was subjected to purification by column chromatography. This gave a white powder (170 mg, 20%).

$^1$H-NMR (CD$_2$Cl$_2$, 500 MHz): 7.23 (1H, CH$_{phenyl}$ or NCHCHN), 7.02 (1H), 6.79 (2H), 6.68 (1H), 6.30 (2H), 5.85 (2H) (each CH$_{phenyl}$ or NCHCHN), 2.21 (3H, CH$_3$), 2.01 (3H, CH$_3$).

$^{13}$C-NMR (CD$_2$Cl$_2$, 125 MHz): 174.8 (NCN), 149.3, 144.2, 137.6, 135.7, 132.3 (each C$_q$ or IrC$_{phenyl}$), 139.6, 127.8, 125.0, 120.2, 120.0, 113.4, 109.1 (CH$_{phenyl}$ or NCHCHN), 20.5, 19.9 (each CH$_3$).

Mass (EI): m/e=934.

Optical spectroscopy: λ=489 nm (main maximum of the powder).

c) Preparation of an Ir Complex (7)

Synthesis Variant I

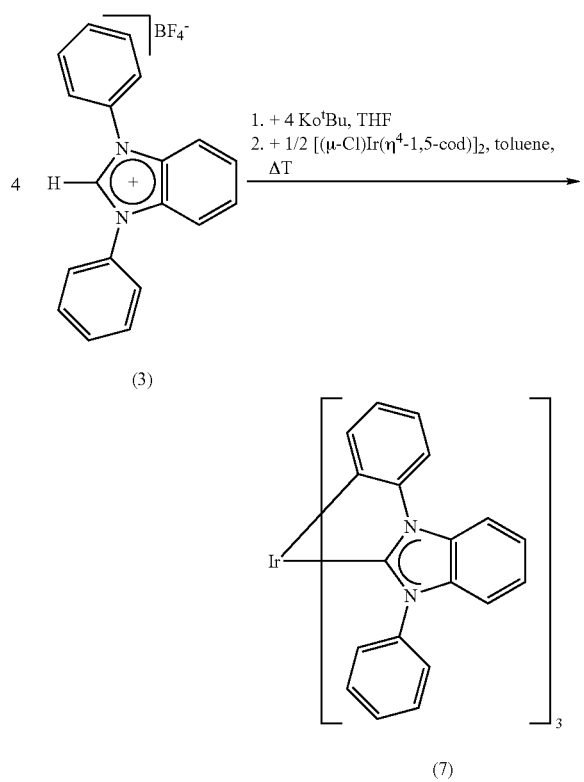

In a 100 ml three-necked flask, 0.99 g (2.8 mmol) of the benzimidazolium salt (compound (3)) was suspended in 20 ml of THF. A solution of 0.32 g of KO$^t$Bu in 10 ml of THF was added to this light yellow suspension at room temperature. The mixture was stirred at room temperature for 45 minutes and subsequently evaporated to dryness. After the residue had been taken up again in 25 ml of toluene, this suspension was added to a solution of 310 mg of [(μ-Cl)(η$^4$-1,5-cod)Ir]$_2$ (0.46 mmol) in 30 ml of toluene. The mixture was subsequently stirred for 15 minutes at room temperature, overnight at 80° C., for 8 hours under reflux, over the weekend at room temperature and for 5 hours under reflux. After cooling, the precipitate was separated off and the filtrate was evaporated. The yellow powder obtained was subjected to purification by column chromatography. This gave a white powder (410 mg, 43%)

Synthesis Variant II 1.32 g (3.7 mmol) of the benzimidazolium salt (compound (3)) together with 25 ml of toluene were placed in a 100 ml three-neck flask. 7.5 ml of potassium bistrimethylsilylamide (0.5 M in toluene, 3.7 mmol) were added at room temperature over a period of 30 minutes and the mixture was stirred at room temperature for 30 minutes. 310 mg (0.46 mmol) of [(μ-Cl)(η$^4$-1,5-cod)Ir]$_2$ were dissolved in 30 ml of toluene and the salt mixture was added dropwise at room temperature. The mixture was stirred at room temperature for one hour, then at 70° C. for two hours and subsequently overnight under reflux. After filtration, the solution was evaporated to dryness and the brown residue was subjected to purification by column chromatography. This gave a white powder (0.75 g, 82%).

The Ir complex (7) is formed as a mixture of the kinetically preferred meridional (mer) isomer and the thermodynamically preferred facial (fac) isomer.

$^1$H-NMR (fac/mer isomer mixture, data for the main isomer (fac isomer), CDCl$_3$, 500 MHz): 8.03 (d, 1H), 7.85 (d, 1H), 7.21 (m, 2H), 7.01 (m, 1H), 6.93 (m, 1H), 6.65 (m, 1H), 6.61 (m, 1H), 6.53 (m, 1H), 6.47 (m, 1H), 6.35 (d, 1H), 6.20 (m, 1H), 6.11 (m, 1H) each (CH$_{aryl}$ or NCHCHN).

$^{13}$C-NMR (fac/mer isomer mixture, data for the main isomer (fac isomer), CDCl$_3$, MHz): 187.8 (NCN), 148.8, 147.8, 137.2, 136.9, 131.7 (each C$_q$ or IrC$_{phenyl}$), 135.9, 127.8, 127.3, 127.0, 126.6, 126.4, 123.6, 121.9, 120.8, 120.3, 111.6, 109.9, 109.5 (CH$_{aryl}$).

Mass (fac/mer isomer mixture, EI): m/e=1000.0.

Elemental analysis (fac/mer isomer mixture, IrC$_{54}$H$_{39}$N$_6$ 3/4CH$_2$Cl$_2$): C, 65.2%, H, 3.8%, N, 7.9%, Cl, 5.0; found: C, 64.8%, H, 4.0%, N, 8.1%, Cl, 4.9%.

Optical spectroscopy: λ=467 nm (fac/mer isomer mixture, main maximum of the powder)

DTA (fac/mer isomer mixture): Rapid decomposition occurred at about 350° C. when the measurement was carried out in air. Decomposition of the sample commences at about 380° C. under inert gas. (Measurement conditions: in air: 28.0/5.0 (K/min)/750.0, under inert gas: 30.0/5.00 (K/min)/710).

d) Chromatography, Separation of the fac and mer Isomers of the Ir Complex of the Formula (7)

The TLC (eluent: toluene) shows 2 spots, with the fac isomer running at R$_F$=0.5 and the mer isomer running at about R$_F$=0.35.

0.46 g of the material to be separated were dissolved in toluene with addition of a small amount of CH$_2$Cl$_2$ and heating to about 30-40° C.

The two isomers were subsequently separated chromatographically with small fractionation on silica gel (0.063-0.200 mm J. T. Baker) using toluene as eluent (dimensions of the column: length: 30 cm, diameter: 6 cm).

Amount of fac isomer obtained: 0.2886 g $^1$H-NMR (CD$_2$Cl$_2$, 500 MHz) (fac):

δ=8.10 (d, 3H), 7.94 (d, 3H), 7.28 (m, 6H), 7.06 (m, 3H), 7.02 (m, 3H), 6.74 (m, 3H), 6.68 (m, 3H), 6.60 (d, 3H), 6.56 (d, 3H), 6.42 (d, 3H), 6.29 (m, 3H), 6.18 (d, 3H).

mer isomer: 0.0364 g $^1$H-NMR (CD$_2$Cl$_2$, 500 MHz, −20° C.) (mer):

δ=8.30 (d, 1H), 7.89 (m, 2H), 7.73 (d, 1H), 7.56 (d, 1H), 7.31 (d, 1H), 7.28-7.16 (m, 5H), 7.08-7.01 (m, 3H), 6.98 (m, 1H), 6.93 (m, 1H), 6.85-6.20 (m, 21H), 5.78 (d, 1H), 5.64 (d, 1H).

e) Preparation of an Ir Complex (8)

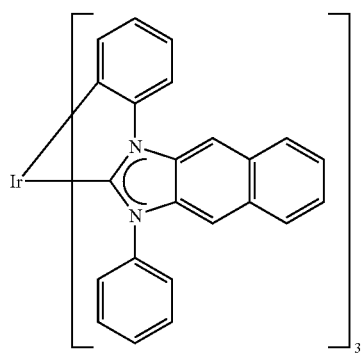

1.51 g (3.7 mmol) of the naphthimidazolium salt together with 40 ml of toluene were placed in a 100 ml three-neck flask. 7.4 ml of potassium bis(trimethylsilyl)amide (0.5 M in toluene, 3.7 mmol) were added at RT over a period of 30 minutes and the mixture was stirred at room temperature for 30 minutes. 310 mg (0.46 mmol) of $[(\mu\text{-Cl})(\eta^4\text{-1,5-cod})Ir]_2$ were dissolved in 30 ml of toluene and the salt mixture was added dropwise at room temperature. The mixture was stirred at room temperature for one hour, then at 70° C. for two hours and then overnight under reflux. The mixture was evaporated to dryness and the brown residue was subjected to purification by column chromatography. This gave a light yellow powder (0.37 g, 35%).

$^1$H-NMR (fac/mer isomer mixture, data for the main isomer (fac isomer)): ($CD_2Cl_2$, 500 MHz): δ=8.47 (s, 1H), 8.05 (m, 2H), 7.57 (d, 1H), 7.41 (m, 1H), 7.33 (d, 1H), 7.28 (t, 1H), 7.09 (m, 1H), 6.75 (s, 1H), 6.69 (d, 1H), 6.64 (t, 1H) 6.57 (d, 1H), 6.52 (m, 1H), 6.24 (m, 2H).

$^{13}$C-NMR (fac/mer isomer mixture, data for the main isomer (fac isomer)): ($CD_2Cl_2$, 125 MHz): δ=193.9 (NCN), 146.67, 137.6, 136.9, 131.4, 129.5, 128.4 (C), 135.7, 128.2, 127.5, 127.4, 127.3, 127.0, 126.8, 126.7, 124.2, 124.0, 123.7, 120.7, 111.8, 106.2, 105.4 (CH).

Mass (EI): m/e=1151 (M-H+).

Elemental analysis (fac/mer isomer mixture, $IrC_{69}H_{45}N_6$ $1/2CH_2Cl_2$): C, 70.0%, H, 3.9%, N, 7.1%, Cl, 5.0; found: C, 69.9%, H, 4.2%, N, 7.0%.

DTA: decomposition occurred above about 360° C. in the measurement in air (measurement conditions: 35.0/5.0 (K/min)/720.0).

f) Crystal Structure Analysis of the fac Isomer of the Ir Complex (7)

Figure 2:
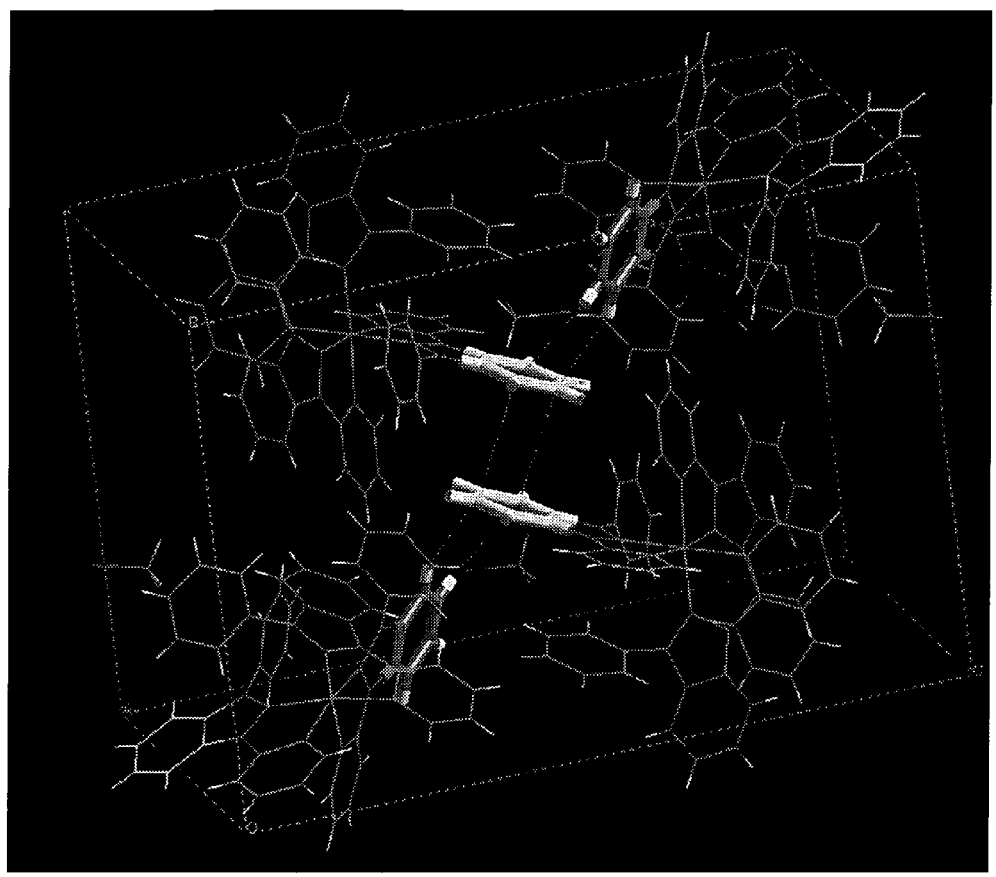
FIG. 2 shows the crystal structure of the fac isomer of the Ir complex (7).

Crystals suitable for X-ray structure analysis were obtained under an inert gas atmosphere by slow diffusion of pentane into a solution of a fac/mer isomer mixture of the Ir complex (7) in methylene chloride. FIG. 2 shows the crystal structure of the fac isomer of the Ir complex (7). The lengths of the Ir-carbene carbon bonds of the three ligands are 2.034 Å, 1.997 Å and 2.025 Å and thus each correspond to an Ir—C single bond. The pairing of in each case two molecules of the Ir complex (7) via one of the fused-on phenyl rings of each is conspicuous. The average distance between the participating phenyl ring planes is 3.6 Å.

g) Optical Spectroscopy of the Ir Complex (7)

ga) Measurement of Optical Properties as a Function of the Isomer Ratio

Samples of the Ir complex (7) were measured in a concentration of 2 mg/l in toluene ("spectroscopic grade"). Various samples having different fac-mer isomer ratios were examined.

gaa) Samples

The following samples having different isomeric purities were characterized in terms of their optical properties (table 1) and compared below.

TABLE 1

Composition of the samples for optical spectroscopy

| Sample # | | fac/mer ratio |
|---|---|---|
| 1 | from example 2c | 9:1[a] |
| 2 | removal of the fac isomer by sublimation[c] | 2:1[a] |
| 3 | by column chromatography | 29:1[b] |
| 4 | (example 2d) | 1:37[b] |

[a] Ratio according to $^1$H-NMR
[b] Ratio according to HPLC
[c] Sublimation is carried out in a high vacuum unit (preliminary diaphragm pump, molecular turbopump) at p = 1 × 10$^{-5}$ mbar. The appropriate amount of the substance was placed in a reservoir, the apparatus was carefully evacuated and the temperature was gradually increased. The sublimation was carried out as a fractional sublimation.

gab) Absorption Spectra of the Ir Complex (7) in Toluene

Normalized absorption spectra of the samples 1 to 4 in toluene were measured. The spectra of the crude Ir complex (7) (sample 1) and sample 2 in toluene solution cannot be distinguished. The fac isomer (sample 3) is hypsochromically shifted by 6 nm compared to the mer isomer (sample 4) and clearly shows a shoulder at 335 nm. Mathematical superposition of the fac and mer spectra in a ratio of 80/20 is virtually identical to the absorption spectrum of the starting sample (sample 1). This confirms that the starting mixture comprises the two isomers in the weighted ratio $z_{fac}/z_{mer}$ of 80/20.

A normalized absorption spectrum corresponds to the measured optical density relative to the optical density at the absorption maximum; it is concentration-independent and describes only the line shape.

$$OD_i^{norm}(\lambda) = \frac{OD_i(\lambda)}{OD_i^{max}(\lambda_{max})} = \frac{\varepsilon_i(\lambda)}{\varepsilon_i^{max}}$$

In the mathematical superposition:

$$OD_{cal}^{norm}(\lambda) = \frac{OD_{fac}^{max}OD_{fac}^{norm}(\lambda) + OD_{mer}^{max}OD_{mer}^{norm}(\lambda)}{OD_{fac}^{max} + OD_{mer}^{max}} N_{norm}$$

$$= (z_{fac}OD_{fac}^{norm}(\lambda) + z_{mer}OD_{fac}^{norm}(\lambda))N_{norm}$$

where $$z_{fac} + z_{mer} = 1$$

and $$z_{fac} = \frac{OD_{fac}^{max}}{OD_{fac}^{max} + OD_{mer}^{max}}$$

The values $z_{fac}$ and $z_{mer}$ are the proportions weighted according to the optical density at the absorption maximum and depend on the product of the maximum molar extinction coefficient $\varepsilon_{max}$ and the concentration. They are not identical to the mole fractions. These can be obtained from $z_{fac}$ and $z_{mer}$ with the aid of the extinction coefficients at the absorption maximum $\varepsilon_{max}$ (fac and mer). The ratio $z_{fac}/z_{mer}$ is the ratio of the optical densities at the absorption maxima. $N_{mer}$ is the normalization factor which guarantees that the summated spectrum is normalized to one.

gac) Emission Spectra of the Ir Complex (7) in Toluene

Normalized emission spectra of the samples 1 to 4 in toluene were measured. In the emission spectra, fac and mer isomers are clearly distinguishable in terms of shape and position of the maxima. The mer spectrum is clearly shifted bathochromically (emission maxima 395 vs. 461 nm). The contribution of the mer isomer in the mixture is shown by the shoulder at 450 nm in the emission spectrum. The emission band of the fac isomer is significantly narrower. Here too, mathematical superposition of the normalized emission spectra of the two isomers in a ratio of 80/20 gives the spectrum of the starting sample.

In the mathematical superposition of normalized emission spectra:

$$I_{norm}^{em}(\lambda) = \frac{OD_{fac}(\lambda_{exc})\Phi_{fac}I_{fac}^{norm}(\lambda) + OD_{mer}(\lambda_{exc})\Phi_{mer}I_{mer}^{norm}(\lambda)}{OD_{fac}(\lambda_{exc})\Phi_{fac} + OD_{mer}(\lambda_{exc})\Phi_{mer}}N_{norm}$$

$$= (y_{fac}(\lambda_{exc})I_{fac}^{norm}(\lambda) + y_{mer}(\lambda_{exc})I_{mer}^{norm}(\lambda))N_{norm}$$

where $$y_{fac}(\lambda_{exc}) + y_{mer}(\lambda_{exc}) = 1$$

and $$y_{fac}(\lambda_{exc}) = \frac{OD_{fac}(\lambda_{exc})\Phi_{fac}}{OD_{fac}(\lambda_{exc})\Phi_{fac} + OD_{mer}(\lambda_{exc})\Phi_{mer}}$$

The values $y_{fac}$ and $y_{mer}$ depend on the excitation wavelength and indicate the proportions of the total emission weighted according to the emission intensity (=product of bsorption at the excitation wavelength OD ($\lambda_{exc}$) and quantum yield ϕ). They are not identical to the mole fractions. These can be obtained from $y_{fac}$ and $Y_{mer}$ with the aid of the extinction coefficients at the absorption maximum $\epsilon_{max}$ (fac and mer) and the quantum yields of the two isomers. $N_{mer}$ is the normalization factor which guarantees that the summated spectrum is normalized to one.

The measured photoluminescence quantum yields of the four samples in toluene do not vary, both in air-saturated solution and under nitrogen (table 2).

TABLE 2

Quantum yields of the photoluminescence of the Ir complex (7) in toluene.

|  | QY[1]/%, air-saturated toluene Exc[2] 325 nm | QY[1]/%, nitrogen-saturated toluene Exc[2] 325 nm |
|---|---|---|
| Sample 1 | 0.6 | 1.3 |
| Sample 2 | 0.6 | 1.4 |
| Sample 3 (fac) | 0.6 | 1.3 |
| Sample 4 (mer) | not determined | 1.4 |

[1]QY = quantum yield
[2]Exc = excitation wavelength

Compared to measurements in a solid matrix (for example PMMA or diphenyldi-o-tolylsilane (UGH 1)), the emitter displays a luminescence quantum yield in nitrogen-saturated solution which is smaller by an order of magnitude. This influence of quenching by solvent molecules is also reflected in the luminescence decay times of the Ir complex (7): in toluene, nitrogen-saturated: 26.5 ns or 25.8 ns vs. 10% of the complex (7) in UGH 1:234 ns. The low sensitivity to oxygen is conspicuous. This can be explained by the luminescence decay time in toluene which is short for a triplet emitter. Given the solubility of oxygen in toluene (1.97 10$^{-3}$ mol/l) and a decay time of about 26 ns, the bimolecular quenching by oxygen is not very effective. However, the decay time in the solid of 230-250 ns is quite short for a triplet emitter and points to effective spin-orbit coupling.

gad) Measurement of Absorption and Emission Spectra at Different fac/mer Isomer Ratios of the Ir Complex (7) in PMMA Films To characterize samples 1 to 4 of the Ir complex (7) further as a diluted solid, corresponding PMMA films were produced. To produce the PMMA film, 2 mg of dye (Ir complex (7), examples 2c and 2d) were dissolved in 1 ml of 10% strength (percent by mass) PMMA solution (PMMA in CH$_2$Cl$_2$) and a film was applied to a microscope slide by means of a 60 μm doctor blade. The film dries immediately. The measurements in toluene (spectroscopic grade) were carried out at a concentration of 10 mg/l. To remove the oxygen in the solution, nitrogen (O$_2$ content <150 ppm) was passed through the solution for 5 minutes before the measurement and nitrogen was passed over the surface of the liquid during the measurement. All measurements were carried out at room temperature.

Absorption:

The fac isomer (example 2d) displays a significant hypsochromic shift in the absorption compared to the mer isomer (example 2d) and has a shoulder at 330 nm. The 80/20 superposition of the fac/mer spectra is identical to the absorption spectra of the starting sample. A somewhat conspicuous aspect is the increased absorption of sample 2 by 280 nm. It must not be forgotten here that the absorption spectra are normalized spectra which show only the spectral shape and not the absolute absorption intensity.

Emission

The emission spectrum of sample 3 is, as before in toluene and in the powder, significantly narrower and pure blue. Sample 4 has the maximum at 460 nm with a shoulder at 400-410 nm. Here too, a mathematical superposition (80/20) reproduces the spectrum of the mixture.

The spectra in PMMA largely correspond to those in toluene. However, quenching of the phosphorescence emission plays a role in the solution spectra, which has no influence on the emission spectra but reduces the photoluminescence quantum yield. Table 3 below shows the quantum yields of the 4 samples in PMMA films and the color coordinates.

TABLE 3

Photoluminescence quantum yields and color coordinates in PMMA.

| Sample # | QY[1]/% in PMMA Exc[2] 325 nm | $X_{RGB}$ in PMMA CIE 1931 | $Y_{RGB}$ in PMMA CIE 1931 |
|---|---|---|---|
| Sample 1 | 19 | 0.160 | 0.078 |
| Sample 2 | 15 | 0.160 | 0.080 |
| Sample 3 (fac) | 17 | 0.160 | 0.047 |
| Sample 4 (mer) | 11 (exc 330 nm) | 0.164 | 0.165 |

[1]QY = quantum yield
[2]Exc = excitation wavelength

The quantum yield of sample 4 is significantly lower than those of the 3 other samples. In the case of films and at these numerical values, the accuracy of the measurement of the quantum yields is in the region of 2 percentage points, i.e. significantly less accurate than in solution because a film gives poorer definition compared to a solution because it is less homogeneous.

gae) Summary of the Optical Characterization of Complex (7)

The studies show that the fac isomer and the mer isomer of the Ir complex (7) differ significantly in terms of their spectroscopic properties. Fac-(7) has a photoluminescence quantum yield in the solid of about 20%, which is virtually twice as high as that of mer-(7). While fac-(7) emits in the pure blue region, the emission of mer-(7) extends into turquoise-colored regions. On the basis of the positions of the emission and absorption bands, nonradiated energy transfer from the fac to mer isomer should be possible (virtually not at all in the opposite direction), so that at application-relevant degrees of doping or emitter molecule spacings, any contamination by mer-(7) partly quenches the emission of the fac isomer, independently of the action of the mer isomer as a trap for individual charges. The additional mer emission resulting therefrom has a longer wavelength and is less efficient. This interpretation is supported by the measurement of the concentration dependence of the Ir complex (7) in PMMA films. The use of isomerically pure compounds of the Ir complex (7) is therefore preferred for the construction of devices.

h) Determination of the Quantum Yield and Emission Properties of the Complex (8) in Toluene and PMMA To produce the PMMA film, 2 mg of dye (Ir complex (8)) were dissolved in 1 ml of 10% strength (percent by mass) PMMA solution (PMMA in $CH_2Cl_2$) and a film was applied to a microscope slide by means of a 60 µm doctor blade. The film dries immediately. The measurements in toluene (spectroscopic grade) were carried out at a concentration of 10 mg/l. To remove the oxygen in the solution, nitrogen ($O_2$ content <150 ppm) was passed through the solution for 5 minutes before the measurement and nitrogen was passed over the surface of the liquid during the measurement. All measurements were carried out at room temperature. At an excitation wavelength of 330 nm, the emitter gives a quantum yield of 10% in PMMA and a quantum yield of 3.6% in toluene. The emission maximum in toluene and PMMA is 512 nm. The CIE coordinates in PMMA are $X_{RGB}=0.302$, $Y_{RGB}=0.591$.

3. Device Construction

The electroluminescence of the complex (7) (cf. examples 2c, 2d) and of the complex (8) (cf. example 2e) were in each case tested in a device having the following layer structure:

3a) Construction of a Device Comprising Complex (7) as Emitter Substance

The ITO substrate used as anode is firstly cleaned by boiling in isopropanol and acetone. At the same time, it is treated with ultrasound. Finally, the substrates are cleaned in a dishwasher using commercial cleaners for LCD production (Deconex® 20NS and neutralization agent 25ORGANACID®). To eliminate any remaining organic residues, the substrate is exposed to a continuous flow of ozone for 25 minutes. This treatment also improves hole injection, since the work function of the ITO is increased.

PEDT:PSS (poly(3,4-ethylenedioxythiophene)-poly(styrene sulfonate)) (Baytron® P VP Al 4083) is subsequently applied to the specimen from aqueous solution by spin coating. A thickness of 46 nm is obtained. This is followed by the emitter layer which is composed of PMMA (polymethyl methacrylate) dissolved in chlorobenzene and the emitter substance (complex (7), example 2c, example 2d). A twenty percent strength by weight solution of PMMA in chlorobenzene is used. The dopant (emitter) is added thereto in various concentrations.

The 28% strength solution gives a thickness of about 61 nm after application by spin coating and the 40% strength solution gives a thickness of 77 nm. These solutions were prepared using an isomer mixture (fac/mer) of the emitter in which the facial isomer is the main component (example 2c). Furthermore, a 30% strength solution was prepared using the isomerically pure fac emitter (example 2d). After application by spin coating, this solution gives a layer thickness of 27 nm.

To balance the charge carriers better, 40 nm of BCP (2,9-dimethyl-4,7-diphenyl-1,10-phenanthroline) are then applied by vapor deposition. BCP is known for its good conductivity for electrons, and it also, owing to its low HOMO, blocks holes which can thus leave the PMMA only with difficulty. Finally, 1 nm of lithium fluoride and 130 nm of aluminum are deposited as cathode.

To characterize the component (OLED), electroluminescence spectra are then recorded at various currents and voltages. In addition, the current-voltage curve is measured in combination with the luminous power of the emitted light. The luminous power can then be converted into photometric parameters by calibration with a luminance meter.

The following electrooptical data are thus obtained for the above-described components (OLEDs):

| Device | PMMA layer thickness | Emission maximum | Photometric efficiency | External quantum yield | Luminance |
|---|---|---|---|---|---|
| 28% of complex 7 (fac/mer)[1] | 61 nm | 453 nm | 0.8 cd/A | 1% | 30 cd/m$^2$ |
| 40% of complex 7 (fac/mer)[1] | 77 nm | 453 nm | 0.65 cd/A | 0.75% | 75 cd/m$^2$ |
| 30% of complex 7 (pure fac)[2] | 27 nm | 400 nm | 0.53 cd/A | 1.5% | 80 cd/m$^2$ |

[1]Example 2c
[2]Example 2d

3b) Construction of a Device Comprising Complex (8) as Emitter Substance

The ITO substrate used as anode is firstly cleaned with isopropanol at 30° C. in an ultrasonic bath for 10 minutes and then cleaned with chloroform, likewise at 30° C. in an ultrasonic bath, for 10 minutes. The substrate is then treated in an oxygen plasma for 20 minutes to eliminate any remaining organic residues.

NPD is then vapor-deposited as hole conductor onto the substrate at $2\times10^{-5}$ mbar and a deposition rate of 0.2 Å/s, so that a layer thickness of 40 nm is obtained. Complex (8) (example 2e) as 5% strength dopant is subsequently vapor-deposited together with the matrix material CBP. The thickness of this layer is likewise 40 nm. This is followed by the BCP hole-blocking layer (6 nm) and an electron conductor layer comprising $Alq_3$ having a thickness of 20 nm. Finally, a 1 nm thick LiF layer is applied and the Al electrode is finally vapor-deposited.

A photometric efficiency of 6.4 cd/A at an emission maximum of 513 nm is obtained for the above-described component (OLED). The maximum luminance is 1487 cd/m$^2$.

We claim:

1. An organic light-emitting diode comprising at least one uncharged transition metal complex of the formula (I) comprising at least one carbene ligand

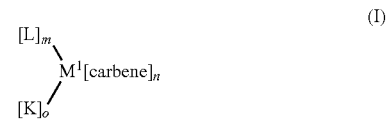

wherein the symbols have the following meanings:
$M^1$ is Ir in any oxidation state possible;
carbene is a carbene ligand selected from the group consisting of the following formulae

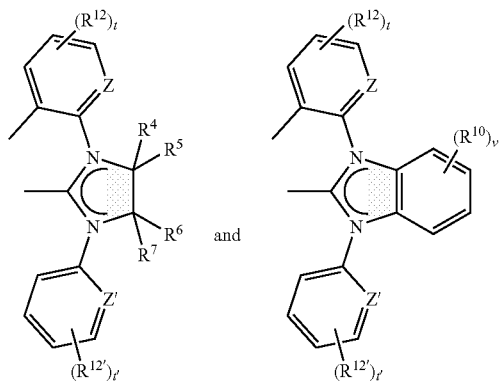 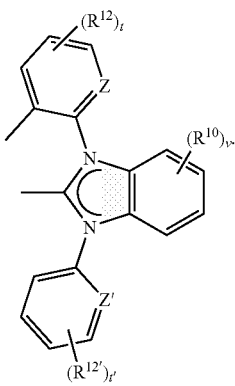

wherein Z, Z' are identical or different and are each CH or N;

$R^{12}, R^{12'}$ are identical or different and are each an alkyl, aryl, heteroaryl or alkenyl radical, or 2 radicals $R^{12}$ or $R^{12'}$ together form a fused-on ring which may contain at least one heteroatom, or $R^{12}$ or $R^{12'}$ is a radical which acts as a donor or acceptor;

t and t' are identical or different and are each from 0 to 3, and when t or t'>1 the radicals $R^{12}$ or $R^{12'}$ can be identical or different;

$R^4$, $R^5$, $R^6$, and $R^7$ are each hydrogen, alkyl, aryl, heteroaryl or alkenyl or a radical which acts as a donor or acceptor;

$R^{10}$ is alkyl, aryl, heteroaryl or alkenyl or 2 radicals $R^{10}$ together form a fused-on ring which may contain at least one heteroatom, or $R^{10}$ is a radical which acts as a donor or acceptor; and v is from 0 to 4 and when v is 0 the four carbon atoms of the aryl radical in the formula c which may be substituted by $R^{10}$ bear hydrogen atoms;

L is a monoanionic or dianionic ligand, which may be monodentate or bidentate;

K is an uncharged monodentate or bidentate ligand selected from the group consisting of phosphines; phosphonates and derivatives thereof, arsenates and derivatives thereof; phosphites; CO; pyridines; nitriles and conjugated dienes which form a π complex with $M^1$;

n is the number of carbene ligands, wherein n is at least 1 and when n>1 the carbene ligands in the complex of the formula I can be identical or different;

m is the number of ligands L, wherein m can be 0 or ≧1 and when m>1 the ligands L can be identical or different;

o is the number of ligands K, wherein o can be 0 or ≧1 and when o>1 the ligands K can be identical or different;

wherein the sum n+m+o is dependent on the oxidation state and coordination number of the metal atom and on the denticity of the ligands carbene, L and K and also on the charge on the ligands carbene and L, with the proviso that n is at least 1.

2. The organic light-emitting diode as claimed in claim 1, wherein the uncharged transition metal complexes are employed as emitter molecules.

3. The organic light-emitting diode as claimed in claim 1, wherein the carbene ligand is:

4. An uncharged transition metal complex of the formula:

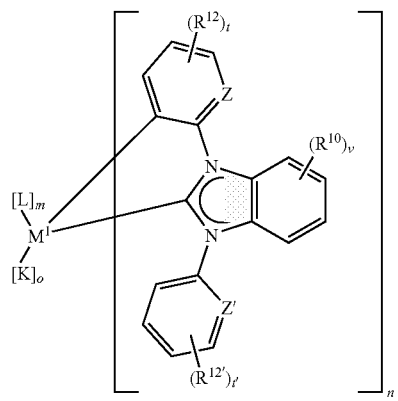

wherein the symbols have the following meanings:

$M^1$ is Ir in any oxidation state possible;

L is a monoanionic or dianionic ligand, which may be monodentate or bidentate;

K is an uncharged monodentate or bidentate ligand;

n is the number of carbene ligands, wherein n is at least 2 and the carbene ligands in the transition metal complex can be identical or different;

m is the number of ligands L, wherein m can be 0 or ≧1 and when m>1 the ligands L can be identical or different;

o is the number of ligands K, wherein o can be 0 or ≧1 and in the case of o>1 the ligands K can be identical or different;

wherein the sum n+m+o is dependent on the oxidation state and coordination number of the metal atom used and the denticity of the ligands and also on the charge on the ligands, with the proviso that n is at least 2; and wherein the following symbols have the following meanings:

Z, Z' are identical or different and are each CH or N;

$R^{12}$, $R^{12'}$ are identical or different and are each an alkyl, aryl, heteroaryl or alkenyl radical, or 2 radicals $R^{12}$ or $R^{12'}$ together form a fused-on ring which may contain at least one heteroatom, or $R^{12}$ or $R^{12'}$ is a radical which acts as a donor or acceptor;

t and t' are identical or different and are each from 0 to 3, and when t or t'>1 the radicals $R^{12}$ or $R^{12'}$ can be identical or different;

$R^{10}$ is alkyl, aryl, heteroaryl or alkenyl or 2 radicals $R^{10}$ together form a fused-on ring which may contain at least one heteroatom, or $R^{10}$ is a radical which acts as a donor or acceptor; and v is from 0 to 4 and when v is 0 the four carbon atoms of the aryl radical in the formula c which may be substituted by $R^{10}$ bear hydrogen atoms.

5. The uncharged transition metal complex as claimed in claim 4, wherein $M^1$ is Ir(III), n is 3 and m and o are each 0, and wherein the three carbene ligands are identical.

6. A process for preparing transition metal complexes as claimed in claim 4 by the deprotonation of the ligand precursors corresponding to the appropriate carbene ligands and subsequent reaction with suitable metal complexes in which the desired metal is present.

7. An OLED comprising at least one transition metal complex as claimed in claim 4.

8. A light-emitting layer comprising at least one transition metal complex of the formula (I) comprising at least one carbene ligand

(I)

wherein the symbols have the following meanings:
$M^1$ is Ir in any oxidation state possible;
carbene is a carbene ligand selected from the group consisting of the following formulae

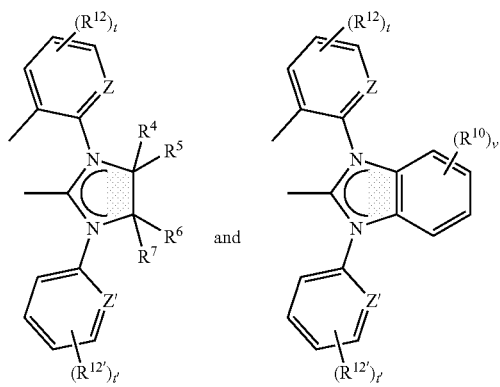

wherein Z, Z' are identical or different and are each CH or N;
$R^{12}, R^{12'}$ are identical or different and are each an alkyl, aryl, heteroaryl or alkenyl radical, or 2 radicals $R^{12}$ or $R^{12'}$ together form a fused-on ring which may contain at least one heteroatom, or $R^{12}$ or $R^{12'}$ is a radical which acts as a donor or acceptor;
t and t' are identical or different and are each from 0 to 3, and when t or t' >1 the radicals $R^{12}$ or $R^{12'}$ can be identical or different;
$R^4$, $R^5$, $R^6$, and $R^7$ are each hydrogen, alkyl, aryl, heteroaryl or alkenyl or a radical which acts as a donor or acceptor;
$R^{10}$ is alkyl, aryl, heteroaryl or alkenyl or 2 radicals $R^{10}$ together form a fused-on ring which may contain at least one heteroatom, or $R^{10}$ is a radical which acts as a donor or acceptor; and v is from 0 to 4 and when v is 0 the four carbon atoms of the aryl radical in the formula c which may be substituted by $R^{10}$ bear hydrogen atoms;
L is a monoanionic or dianionic ligand, which may be monodentate or bidentate;
K is an uncharged monodentate or bidentate ligand selected from the group consisting of phosphines; phosphonates and derivatives thereof, arsenates and derivatives thereof; phosphites; CO; pyridines; nitriles and conjugated dienes which form a π complex with $M^1$;
n is the number of carbene ligands, wherein n is at least 1 and when n>1 the carbene ligands in the complex of the formula I can be identical or different;
m is the number of ligands L, wherein m can be 0 or ≧1 and when m>1 the ligands L can be identical or different;
o is the number of ligands K, wherein o can be 0 or ≧1 and when o>1 the ligands K can be identical or different;
wherein the sum n+m+o is dependent on the oxidation state and coordination number of the metal atom and on the denticity of the ligands carbene, L and K and also on the charge on the ligands carbene and L, with the proviso that n is at least 1.

9. An OLED comprising a light-emitting layer as claimed in claim 8.

10. A device selected from the group consisting of stationary VDUs, VDUs in printers, kitchen appliances and advertising signs, lighting units, information signs, and mobile VDUs comprising an organic light-emitting diode as claimed in claim 1.

11. A light-emitting layer comprising at least one transition metal complex as claimed in claim 4.

12. An OLED comprising a light-emitting layer as claimed in claim 11.

13. A device selected from the group consisting of stationary VDUs, VDUs in printers, kitchen appliances and advertising signs, lighting units, information signs, and mobile VDUs comprising an OLED as claimed in claim 7.

14. A device selected from the group consisting of stationary VDUs, VDUs in printers, kitchen appliances and advertising signs, lighting units, information signs, and mobile VDUs comprising an OLED as claimed in claim 9.

15. A device selected from the group consisting of stationary VDUs, VDUs in printers, kitchen appliances and advertising signs, lighting units, information signs, and mobile VDUs comprising an OLED as claimed in claim 12.

16. The organic light-emitting diode as claimed in claim 1, wherein the carbene ligand is:

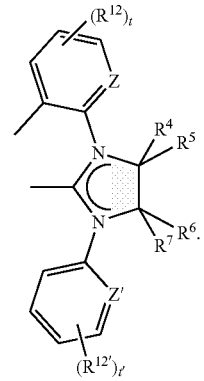

* * * * *